US011090882B2

(12) United States Patent
Saini et al.

(10) Patent No.: US 11,090,882 B2
(45) Date of Patent: Aug. 17, 2021

(54) TEST SYSTEM AND METHOD FOR CREATING CONTROLLED AND REPEATABLE OUT-OF-PLANE FIBER DISTORTION IN COMPOSITE LAMINATES

(71) Applicant: The Boeing Company, Chicago, IL (US)

(72) Inventors: Gagandeep Saini, Snohomish, WA (US); Karl M. Nelson, Issaquah, WA (US); William H. Ingram, Puyallup, WA (US)

(73) Assignee: The Boeing Company, Chicago, IL (US)

( * ) Notice: Subject to any disclaimer, the term of this patent is extended or adjusted under 35 U.S.C. 154(b) by 240 days.

(21) Appl. No.: 16/142,093

(22) Filed: Sep. 26, 2018

(65) Prior Publication Data

US 2020/0094497 A1    Mar. 26, 2020

(51) Int. Cl.
*B32B 41/00*     (2006.01)
*B29C 70/54*    (2006.01)
(Continued)

(52) U.S. Cl.
CPC ............. *B29C 70/54* (2013.01); *B29C 70/36* (2013.01); *B29K 2105/0872* (2013.01); *B29K 2307/04* (2013.01)

(58) Field of Classification Search
CPC ....... B29C 70/54; B29C 70/36; B29C 33/307; B29C 33/42; B29C 70/541; B29C 70/56;
(Continued)

(56) References Cited

U.S. PATENT DOCUMENTS 6,096,164 A * 8/2000 Benson ................. B29C 53/602
156/425
7,527,222 B2    5/2009 Biornstad et al.
(Continued)

FOREIGN PATENT DOCUMENTS

DE    102012217373 A1    5/2014
WO    WO2008133748 A2    11/2008
WO       2010037612 A1    4/2010

OTHER PUBLICATIONS

Extended European Search Report (EESR) European Patent Office, dated Feb. 28, 2020, for counterpart Application No. EP19199520.8, Applicant The Boeing Company, 9 pages.
(Continued)

*Primary Examiner* — Michael N Orlando
*Assistant Examiner* — Joshel Rivera

(57) ABSTRACT

In one version there is provided a test system including a layup tool having a layup surface, and two fairing bars attached to the layup surface. The test system includes the composite laminate having a plurality of stacked plies, and positioned between the two fairing bars. The test system includes fiber distortion initiator(s) positioned at one or more locations under, and adjacent to, one or more plies of the plurality of stacked plies. The test system includes two caul plates with a gap in between, and positioned over the composite laminate. When the test system undergoes a pressurized cure process with a vacuum compaction, a restricted outward expansion of the plurality of stacked plies by the fairing bars, and a pressure differential region formed by the one or more fiber distortion initiators at the one or more locations, create the controlled and repeatable out-of-plane fiber distortion in the composite laminate.

20 Claims, 13 Drawing Sheets

(51) Int. Cl.
 *B29C 70/36* (2006.01)
 *B29K 105/08* (2006.01)
 *B29K 307/04* (2006.01)

(58) Field of Classification Search
 CPC ....... B29C 70/543; B29C 70/24; B29C 70/72;
 B29C 70/82; B29K 2105/0872; B29K
 2307/04; G01N 2033/0003; G01N 3/28;
 G01N 2203/0298; G01N 2203/0096;
 G01N 2203/0244; G01N 2203/0082;
 G01B 21/32
 USPC .......................... 156/64, 350, 351, 378, 379
 See application file for complete search history.

(56) References Cited

U.S. PATENT DOCUMENTS

| | | | |
|---|---|---|---|
| 2006/0280927 A1* | 12/2006 | Albright | B32B 27/18 428/304.4 |
| 2008/0148865 A1 | 6/2008 | Mlinar et al. | |
| 2016/0346995 A1* | 12/2016 | Butler | B29C 66/112 |
| 2019/0111636 A1* | 4/2019 | Van Nieuwenhove | B29D 99/0025 |

OTHER PUBLICATIONS

Wang, J., et al., "Experimental Fabrication and Characterization of Out-of-Plane Fiber Waviness in Continuous Fiber-Reinforced Composites", Journal of Composite Materials, 0(0) pp. 1-13, 2012 (from EESR—vol. 46, No. 17, Dec. 16, 2011, pp. 2041-2053, XP055669870, USA, ISSN: 0021-9983, DOI: 10.1177/0021998311429877).

* cited by examiner

TEST SYSTEM AND METHOD FOR CREATING CONTROLLED AND REPEATABLE OUT-OF-PLANE FIBER DISTORTION IN COMPOSITE LAMINATES

BACKGROUND

1) Field of the Disclosure

The disclosure relates generally to test systems and methods for composite structures, and more particularly, to sub-scale level test systems and methods for composite laminates representative of full-scale size parts or structures.

2) Description of Related Art

Composite structures may be used in a wide variety of applications, including in the manufacture of aircraft, due to their high strength-to-weight ratios, corrosion resistance and other favorable properties. In particular, in aircraft manufacturing, composite structures may be used to form the fuselage, wings, tail sections, and other parts of the aircraft. Composite structures are made of composite material typically including fiber plies, such as carbon fiber plies, in woven and non-woven configurations. The fiber plies may be manufactured into composite parts by laminating them together into composite laminates.

During cure, composite parts, such as composite laminates, reduce in thickness or debulk, as compared to their laid-up non-cured state. When a vacuum is applied to a composite laminate laid up on or around a layup tool, a bulk may be reduced, making the composite laminate thinner. Top-most plies or outer plies, sized to a pre-debulk circumference, may be too long and may distort as they are compacted and forced to reposition into a smaller volume. In particular, the debulking process, while making a cylindrical or barrel-shaped section, such as for an aircraft fuselage, may produce out-of-plane fiber distortion, i.e., fiber wrinkling. Such out-of-plane fiber distortion, or wrinkling, above a certain threshold, is unacceptable in composite manufacturing, and may be particularly problematic with composite manufacturing of cylindrical or curved parts.

In attempts to understand and solve out-of-plane fiber distortion issues in manufacturing of composite parts, known systems and methods involve fabricating full scale size parts to create representative out-of-plane fiber distortion of such parts. For example, such full scale size parts may be fabricated multiple times to understand the benefits of variables that may be changed during testing. However, the fabrication of such full scale size parts to create representative out-of-plane fiber distortion is very expensive, labor intensive, and time intensive. Moreover, it has proven difficult to create repeatable representative out-of-plane fiber distortion of full scale size parts on a sub-scale level or test bed, and in particular, with cylindrical or curved parts.

Accordingly, there is a need in the art for a technical solution for creating controlled and repeatable out-of-plane fiber distortion in composite structures, such as composite laminates, on a sub-scale level, that is less costly, less labor intensive, and less time intensive than known systems and methods.

SUMMARY

Example implementations of this disclosure provide for a test system and method for creating controlled and repeatable out-of-plane fiber distortion in composite structures, such as composite laminates, on a sub-scale level. As discussed in the below detailed description, versions of the test system and method for creating controlled and repeatable out-of-plane fiber distortion in composite structures, such as composite laminates, on a sub-scale level, provide significant advantages over known systems and methods.

In one version there is provided a test system for creating controlled and repeatable out-of-plane fiber distortion in a composite laminate. The test system comprises a layup tool having a layup surface. The test system further comprises two fairing bars attached to the layup surface and spaced opposite to one another.

The test system further comprises the composite laminate comprising a plurality of stacked plies. The composite laminate is laid up on the layup surface of the layup tool and positioned between the two fairing bars.

The test system further comprises one or more fiber distortion initiators positioned at one or more locations under, and adjacent to, one or more plies of the plurality of stacked plies. Each of the one or more fiber distortion initiators comprises a structure having a volume that increases a height of a portion of the one or more plies of the plurality of stacked plies stacked over each of the one or more fiber distortion initiators.

The test system further comprises two caul plates positioned over the composite laminate and positioned between the two fairing bars. The two caul plates have a gap in between the two caul plates. When the test system undergoes a pressurized cure process with a vacuum compaction, a restricted expansion of the plurality of stacked plies by the two fairing bars, and a pressure differential region formed by the one or more fiber distortion initiators at the one or more locations, create the controlled and repeatable out-of-plane fiber distortion of the one or more plies of the plurality of stacked plies in the composite laminate at one or more controlled locations in the composite laminate.

In another version there is provided a test system for creating controlled and repeatable out-of-plane fiber distortion in a composite laminate, used for testing purposes and process improvement. The test system comprising a curved layup tool having a layup surface.

The test system further comprises a first fairing bar and a second fairing bar, both attached to the layup surface. The first fairing bar is spaced opposite the second fairing bar in a parallel alignment.

The test system further comprises the composite laminate comprising a plurality of stacked carbon fiber plies. The composite laminate is laid up on the layup surface of the curved layup tool. The composite laminate has a first peripheral end abutting the first fairing bar and has a second peripheral end abutting the second fairing bar.

The test system further comprises one or more fiber distortion initiators positioned at one or more locations under, and adjacent to, one or more carbon fiber plies of the plurality of stacked carbon fiber plies. Each of the one or more fiber distortion initiators comprises a structure having a volume that increases a height of a portion of the one or more carbon fiber plies of the plurality of stacked carbon fiber plies stacked over each of the one or more fiber distortion initiators.

The test system further comprises a first caul plate positioned next to a second caul plate with a gap in between the first caul plate and the second caul plate. The first caul plate and the second caul plate are positioned over the composite laminate and positioned between the first fairing bar and the second fairing bar. The first caul plate and the second caul plate each have an outer side end abutting the first fairing bar and the second fairing bar, respectively.

When the test system undergoes a pressurized cure process with a vacuum compaction, the first fairing bar and the second fairing bar restrict the plurality of stacked carbon fiber plies from expanding outwardly, and the one or more fiber distortion initiators create a pressure differential region at the one or more locations, to form distorted out-of-plane fibers at one or more controlled locations in the one or more carbon fiber plies of the plurality of stacked carbon fiber plies stacked over the one or more fiber distortion initiators. In turn, this creates the controlled and repeatable out-of-plane fiber distortion in the composite laminate, used for testing purposes and process improvement.

In another version there is provided a method for creating controlled and repeatable out-of-plane fiber distortion in a composite laminate. The method comprises the step of assembling a test system.

The test system comprises a layup tool having a layup surface. The test system further comprises two fairing bars attached to the layup surface and spaced opposite to one another. The test system further comprises the composite laminate comprising a plurality of stacked plies. The composite laminate is laid up on the layup surface of the layup tool and is positioned between the two fairing bars. The test system further comprises one or more fiber distortion initiators positioned at one or more locations under, and adjacent to, one or more plies of the plurality of stacked plies. Each of the one or more fiber distortion initiators comprises a structure having a volume that increases a height of a portion of the one or more plies of the plurality of stacked plies stacked over each of the one or more fiber distortion initiators. The test system further comprises two caul plates positioned over the composite laminate and positioned between the two fairing bars. The two caul plates have a gap in between the two caul plates.

The method further comprises the step of curing the test system with a pressurized cure process and a vacuum compaction, to restrict, with the two fairing bars, the plurality of stacked plies from expanding outwardly, and to create, with the one or more fiber distortion initiators, a pressure differential region at the one or more locations. The method further comprises forming distorted out-of-plane fibers at one or more controlled locations in the one or more plies of the plurality of stacked plies stacked over the one or more fiber distortion initiators, to create the controlled and repeatable out-of-plane fiber distortion in the composite laminate.

The features, functions, and advantages that have been discussed can be achieved independently in various versions or embodiments of the disclosure or may be combined in yet other versions or embodiments, further details of which can be seen with reference to the following description and drawings.

BRIEF DESCRIPTION OF THE DRAWINGS

The disclosure can be better understood with reference to the following detailed description taken in conjunction with the accompanying drawings which illustrate exemplary versions or embodiments, but which are not necessarily drawn to scale, wherein.

Each figure shown in this disclosure shows a variation of an aspect of the embodiments presented, and only differences will be discussed in detail.

DETAILED DESCRIPTION

Disclosed versions or embodiments will now be described more fully hereinafter with reference to the accompanying drawings, in which some, but not all of the disclosed versions are shown. Indeed, several different versions may be provided and should not be construed as limited to the versions set forth herein. Rather, these versions are provided so that this disclosure will be thorough and fully convey the scope of the disclosure to those skilled in the art.

Figure 1:
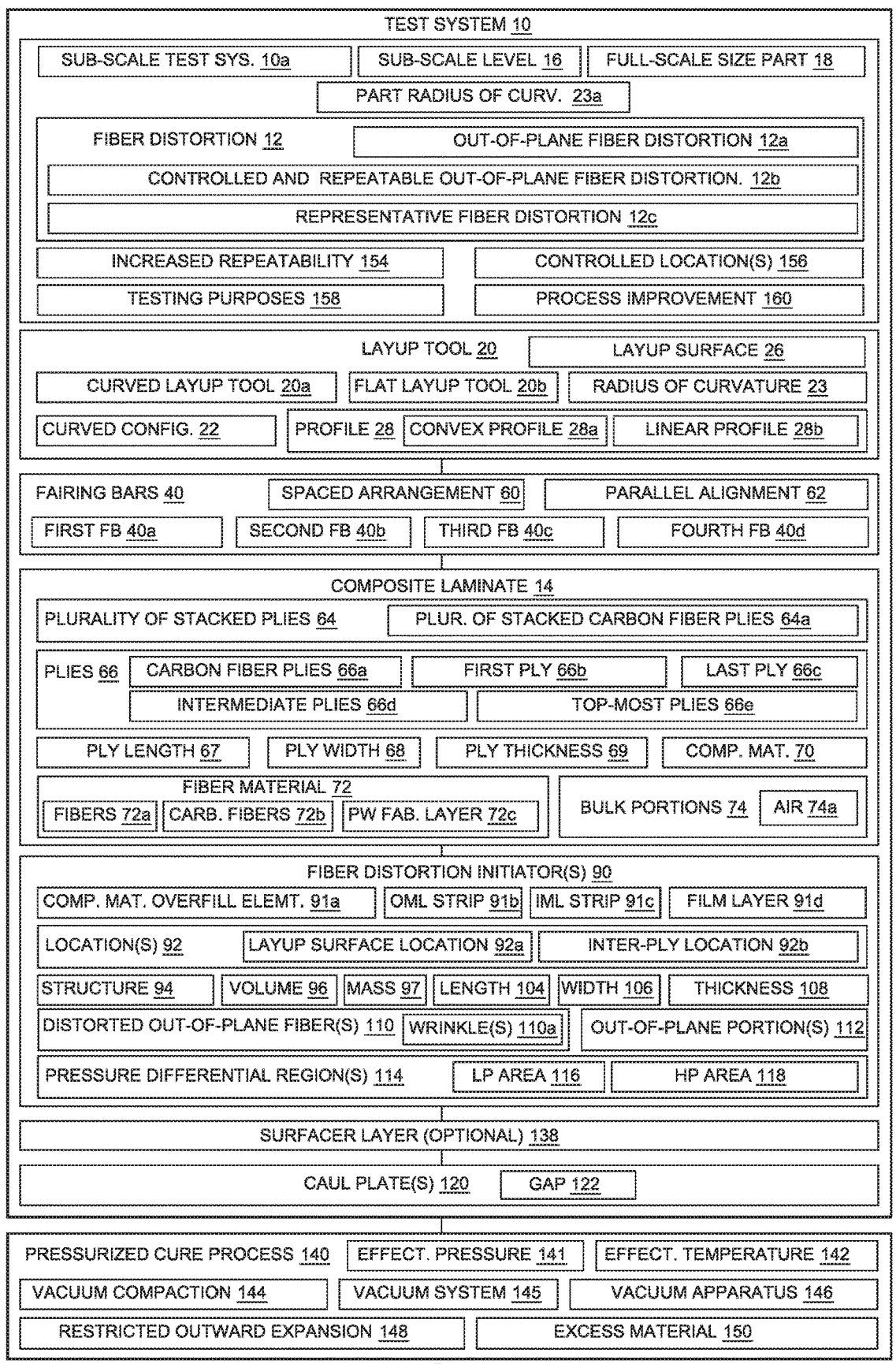
FIG. 1 is an illustration of a functional block diagram showing an exemplary version of a test system of the disclosure.

Now referring to the Figures, FIG. 1 is an illustration of a functional block diagram showing an exemplary version of a test system 10 of the disclosure. The test system 10 (see FIG. 1) is configured to intentionally create, and intentionally creates, fiber distortion 12 (see FIG. 1), including out-of-plane fiber distortion 12a (see FIG. 1), to obtain a controlled and repeatable out-of-plane fiber distortion 12b (see FIG. 1) in a composite laminate 14 (see FIG. 1). As shown in FIG. 1, preferably, the test system 10 is a sub-scale test system 10a for creating and obtaining the controlled and repeatable out-of-plane fiber distortion 12b at a sub-scale level 16, that is a representative fiber distortion 12c of a full-scale size part 18, for example, a fuselage barrel section 220 (see FIG. 7) of a fuselage 202 (see FIG. 7) of an aircraft 200a (see FIG. 7), or another suitable full-scale size part 18, or structure.

As further shown in FIG. 1, the test system 10 and the controlled and repeatable out-of-plane fiber distortion 12b may be used for testing purposes 158 and process improvement 160, for example, for finding solutions to eliminate or minimize fiber distortion 12, such as out-of-plane fiber distortion 12a, in composite structures 218 (see FIG. 7), such as composite laminates 14. The test system 10 (see FIG. 1) facilitates and provides for the intentional creation of distorted out-of-plane fibers 110 (see FIG. 1), also referred to as wrinkles 110a (see FIG. 1), in composite structures 218 (see FIG. 7), such as composite laminates 14 (see FIG. 1). This provides increased repeatability 154 (see FIG. 1) and controlled location 156 (see FIG. 1) of the distorted out-of-plane fibers 110, or wrinkles 110a, in the composite laminate 14. Thus, the test system 10, such as the sub-scale test system 10a, creates the distorted out-of-plane fibers 110, or wrinkles 110a, with increased repeatability 154 on a sub-scale level 16, so that solutions to the problem of formation of distorted out-of-plane fibers 110, or wrinkles 110a, on a full-scale size part 18 can more easily and accurately be solved.

As shown in FIG. 1, the test system 10 comprises a layup tool 20 having a layup surface 26. In one version, the layup tool 20 may comprise a curved layup tool 20a (see FIGS. 1, 4) having a curved configuration 22 (see FIG. 1) and a radius of curvature 23 (see FIG. 1). The curved layup tool 20a (see FIGS. 1, 4) preferably has a profile 28 (see FIGS. 1, 4) comprising a convex profile 28a (see FIGS. 1, 4). As shown in FIG. 1, the full-scale size part 18 may have a part radius of curvature 23a, if the full-scale size part 18 has a curved geometry, for example, the fuselage barrel section 220 (see FIG. 7) of the fuselage 202 (see FIG. 7) of an aircraft 200a (see FIG. 7).

Figure 2A:
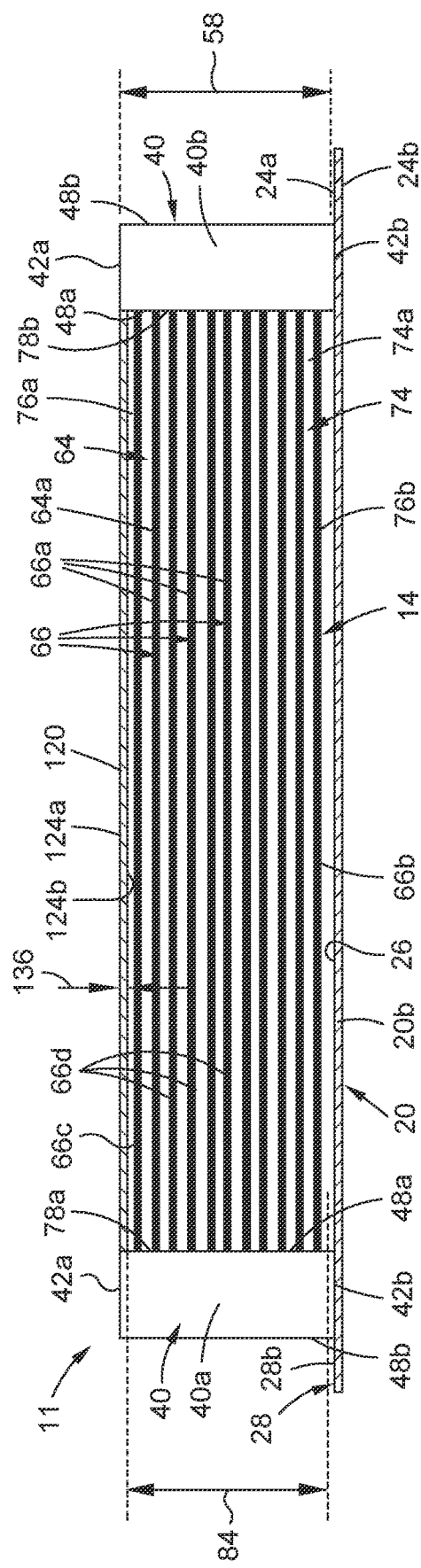
FIG. 2A is an illustration of a front cross-sectional view of a layup setup showing a composite laminate laid up on a layup tool and having no fiber distortion initiators.
Figure 2B:
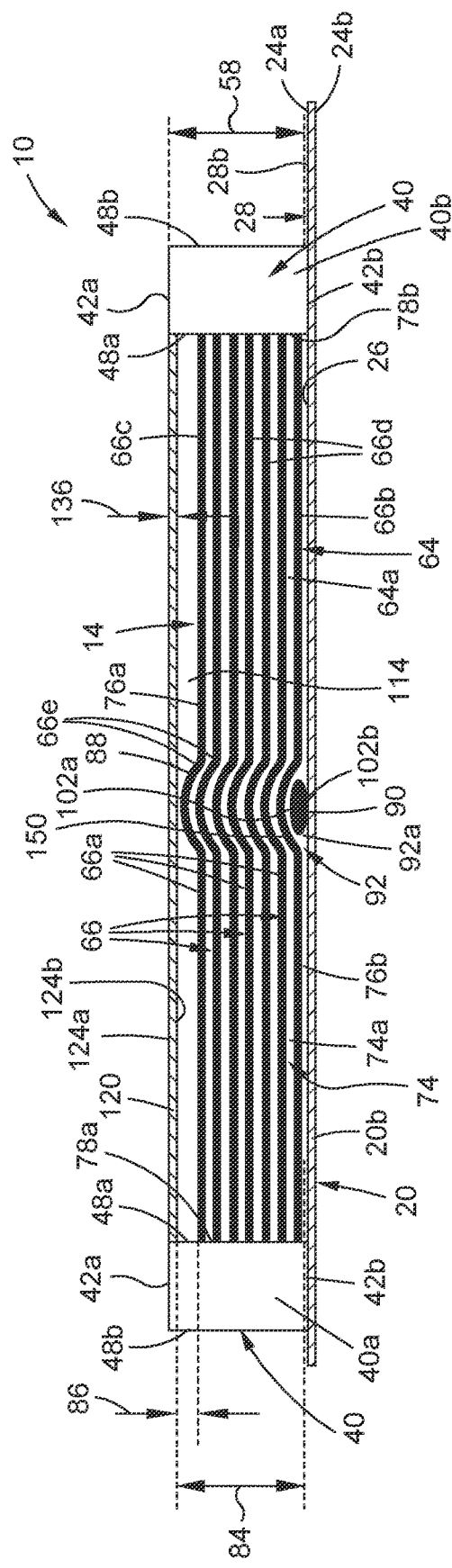
FIG. 2B is an illustration of a front cross-sectional view of a version of a test system of the disclosure with a fiber distortion initiator positioned between a layup tool and a first ply of a plurality of stacked plies.

In another version, the layup tool 20 may comprise a flat layup tool 20b (see FIGS. 1, 2B). The flat layup tool 20b (see FIGS. 1, 2B) has a profile 28 (see FIGS. 1, 2B) comprising a linear profile 28b (see FIGS. 1, 2B).

As shown in FIG. 1, the test system 10 further comprises a plurality of fairing bars 40, such as two fairing bars 40 attached, and preferably removably attached, to the layup surface 26. The plurality of fairing bars 40 function as restrictor beams to restrict or constrain plies 66 (see FIG. 1) of the composite laminate 14 (see FIG. 1) from expanding or stretching outwardly. The two fairing bars 40 are spaced opposite to one another on the layup surface 26 in a spaced arrangement 60 (see FIGS. 1, 3A), and preferably in a parallel alignment 62 (see FIGS. 1, 3A) with each other. The plurality of fairing bars 40, such as the two fairing bars 40, preferably includes a first fairing bar 40a (see FIGS. 1, 3A) and a second fairing bar 40b (see FIGS. 1, 3A). In another version, the plurality of fairing bars 40 may further include a third fairing bar 40c (see FIG. 1) and a fourth fairing bar 40d (see FIG. 1), which may be spaced opposite to one another on the layup surface 26 in the spaced arrangement 60 (see FIG. 1), and preferably in the parallel alignment 62 (see FIG. 1). The use of two fairing bars 40 is preferable. However, if four fairing bars 40 are used, the first fairing bar 40a (see FIG. 1), the second fairing bar 40b (see FIG. 1), the third fairing bar 40c (see FIG. 1), and the fourth fairing bar 40d (see FIG. 1) may be attached to the layup tool 20, and positioned around, and adjacent to, the periphery of the composite laminate 14 configured to be laid up, and subsequently laid up, on the layup tool 20.

The plurality of fairing bars 40 (see FIG. 1), such as the two fairing bars 40, including the first fairing bar 40a (see FIGS. 1, 3A) and the second fairing bar 40b (see FIGS. 1, 3A), are preferably attached, such as removably attached, to the layup surface 26 with one or more attachment elements 52 (see FIGS. 3A, 4), such as one or more fasteners 52a (see FIGS. 3A, 4), such as bolts, or other suitable attachment elements 52. The attachment elements 52 (see FIG. 3A), such as fasteners 52a (see FIG. 3A), are preferably inserted through one or more through openings 50 (see FIG. 3A) formed in each fairing bar 40 (see FIGS. 1, 3A). Alternatively, the plurality of fairing bars 40 may be coupled or removably attached to the layup surface 26 in another suitable manner, for example, with clamps, indexing elements, or the like.

As shown in FIG. 1 the test system 10 further comprises the composite laminate 14. The composite laminate 14 (see FIG. 1) is laid up on the layup surface 26 (see FIG. 1) of the layup tool 20 (see FIG. 1) and positioned between the plurality of fairing bars 40 (see FIG. 1), such as the two fairing bars 40. As shown in FIG. 1, the composite laminate 14 comprises a plurality of stacked plies 64, such as a plurality of stacked carbon fiber plies 64a. The plurality of stacked plies 64, such as the plurality of stacked carbon fiber plies 64a, includes plies 66 (see FIG. 1), or layers, such as carbon fiber plies 66a (see FIG. 1). As shown in FIG. 1, each of the plies 66 has a ply length 67, a ply width 68, and a ply thickness 69. Preferably, the plies 66 are manually laid up within the bounds of the plurality of fairing bars 40, for example, within the bounds of the first fairing bar 40a and the second fairing bar 40b.

The plies 66 preferably comprise one or more composite materials 70 (see FIG. 1), including fiber material 72 (see FIG. 1). As shown in FIG. 1, the fiber material 72 preferably comprises fibers 72a, such as carbon fibers 72b, and/or fabric, such as one or more plain weave (PW) fabric layers 72c. In addition to carbon fibers 72b and the one or more PW fabric layers 72c, exemplary fiber material 72 may include glass fibers, fiberglass, aramids, polymer fibers, synthetic polymer fibers, polypropylene (PP) fibers, nylon fibers, woven fabric, non-woven fabric, a combination of one or more thereof, or other suitable fibers or fabrics.

The plies 66 (see FIG. 1), such as the carbon fiber plies 66a (see FIG. 1), are preferably laid up on the layup surface 26 (see FIG. 1) of the layup tool 20 (see FIG. 1) with bulk portions 74 (see FIG. 1), such as air 74a (see FIG. 1), for example, areas filled with air, such as air pockets, between the plies 66. As shown in FIG. 1, the plies 66 of the composite laminate 14 may include a first ply 66b, or bottom ply, in contact with the layup surface 26 of the layup tool 20; a last ply 66c, or top ply; one or more intermediate plies 66d positioned between the first ply 66b and the last ply 66c; and one or more top-most plies 66e. The carbon fiber plies 66a may comprise carbon fibers in a resin matrix material or a polymer matrix material.

As shown in FIG. 1, the test system 10 further comprises one or more fiber distortion initiators 90, or wrinkle initiators, positioned at one or more locations 92 under, and adjacent to, one or more plies 66 of the plurality of stacked plies 64. As shown in FIG. 1, each of the one or more fiber distortion initiators 90 comprises a structure 94 having a volume 96 and a mass 97. As further shown in FIG. 1, each of the one or more fiber distortion initiators 90 has a length 104, a width 106, and a thickness 108. In one version, each of the one or more fiber distortion initiators 90 (see FIGS. 1, 3B) has a length 104 (see FIGS. 1, 3B) that is substantially equal to a length 80 (see FIG. 3C) of the composite laminate 14 (see FIGS. 1, 3C).

As further shown in FIG. 1, the one or more fiber distortion initiators 90 may comprise a composite material overfill element 91a, an outer mold line (OML) strip 91b, an inner mold line (IML) strip 91c, a film layer 91d, or any number of other suitable fiber distortion initiators 90, depending on the production issue to be solved or the purpose of the testing. For example, a combination of one or more composite material overfill elements 91a, one or more OML strips 91b, and one or more IML strips 91c may all be laid up at a layup surface location 92a (see FIG. 1) on the layup tool 20 and/or at inter-ply locations 92b (see FIG. 1) in the composite laminate 14. Each of the one or more fiber distortion initiators 90 comprises the structure 94 (see FIG. 1) having a volume 96 (see FIG. 1) that increases a height 86 (see FIGS. 2B, 2C) of a portion 88 (see FIGS. 2B, 2C) of the one or more plies 66 (see FIGS. 1, 2B, 2C) of the plurality of stacked plies 64 (see FIGS. 1, 2B, 2C), that are stacked over each of the one or more fiber distortion initiators 90. The one or more fiber distortion initiators 90 may include any structure 94 that increases the height 86 of the portion 88 of the one or more plies 66 in the composite laminate 14, and that creates one or more pressure differential regions 114 (see FIG. 1) with a relative pressure change between a low pressure (LP) area 116 (see FIG. 1) and a high pressure (HP) area 118 (see FIG. 1), at and above the one or more locations 92 (see FIG. 1) of the one or more fiber distortion initiators 90 in the composite laminate 14, and where the height 86 is increased.

In one version of the test system 10, at least one of the one or more fiber distortion initiators 90 (see FIGS. 1, 2B) is positioned in a location 92 (see FIGS. 1, 2B), such as a layup surface location 92a (see FIGS. 1, 2B), adjacent to, and between, the layup surface 26 (see FIGS. 1, 2B) of the layup tool 20 (see FIGS. 1, 2B) and the first ply 66a (see FIGS. 1, 2B), or bottom ply, laid over, and in contact with, the layup surface 26 (see FIGS. 1, 2B) and the at least one fiber distortion initiator 90. In another version of the test system 10, at least one of the one or more fiber distortion initiators 90 (see FIGS. 1, 2C) is positioned in a location 92 (see FIGS. 1, 2C), such as an inter-ply location 92b (see FIGS. 1, 2C), adjacent to, and between, two plies 66 (see FIGS. 1, 2C) of the plurality of stacked plies 64.

As shown in FIG. 1, the test system 10 further preferably comprises two caul plates 120, or caul sheets, with a gap 122 in between the two caul plates 120. The test system 10 may further comprise more than two caul plates 120, or caul sheets, as needed, for example, four, six, eight, or more caul plates 120. The two caul plates 120 are preferably positioned over the composite laminate 14 and positioned between the plurality of fairing bars 40, such as the first fairing bar 40a and the second fairing bar 40b. Preferably, the two caul plates 120 (see FIGS. 1, 3D, 4) comprise a first caul plate 120a (see FIGS. 3D, 4) positioned next to a second caul plate 120b (see FIGS. 3D, 4), with the gap 122 (see FIGS. 1, 3D, 4) in between the first caul plate 120a and the second caul plate 120b, and the gap 122 present prior to the test system 10 undergoing a pressurized cure process 140 (see FIG. 1). As the composite laminate 14 constricts, or shrinks, during the pressurized cure process 140 (see FIG. 1), the two caul plates 120, or more than two caul plates 120, move closer together, since they are restricted on their ends by the respective fairing bars 40, and the gap 122, or gaps 122, in between the two caul plates 120, or more than two caul plates 120, gets smaller or closes up, and allows the two caul plates 120, or more than two caul plates 120, to move closer together without heaving up against each other. The two caul plates 120 (see FIG. 1), or more than two caul plates 120, may be made of steel or another suitable metal material, a ceramic material, a composite material, or other materials designed for curing and consolidation processes to form composite laminates 14.

As shown in FIG. 1, the test system 10 may optionally comprise a surfacer layer 138 (see also FIG. 3D) positioned between the composite laminate 14 and the two caul plates 120, or more than two caul plates 120, for example, directly under the two caul plates 120 and directly over the composite laminate 14. The surfacer layer 138 allows the two caul plates 120, or more than two caul plates 120, to slide over the surfacer layer 138 to create a positional surface. The surfacer layer 138 may comprise a film layer with a bottom side adjacent the composite laminate 14 being tacky or sticky, and a top side adjacent the two caul plates 120 being smooth and non-tacky. Alternatively, the surfacer layer 138 may comprise another type of material layer, depending on where the controlled location 156 (see FIG. 1) of the distorted out-of-plane fiber 110, or wrinkle 110a (see FIG. 1), is intended to be formed in the composite laminate 14, and depending on what production issue is to be solved, and the purpose of the testing.

When the test system 10 undergoes a pressurized cure process 140 (see FIG. 1) with a vacuum compaction 144 (see FIG. 1), the plurality of fairing bars 40, such as the first fairing bar 40a and the second fairing bar 40b, restrict or constrain the peripheral ends or edges of the plurality of stacked plies 64 (see FIG. 1), such as the plurality of stacked carbon fiber plies 64a (see FIG. 1), from expanding outwardly. In addition, when the test system 10 undergoes the pressurized cure process 140 (see FIG. 1) with the vacuum compaction 144 (see FIG. 1), the one or more fiber distortion initiators 90 (see FIG. 1) create the pressure differential region 114 (see FIG. 1) at each of the one or more locations 92 (see FIG. 1), to form distorted out-of-plane fibers 110 (see FIG. 1), such as wrinkles 110a (see FIG. 1), at one or more controlled locations 156 (see FIG. 1), or predetermined or desired locations, in the one or more plies 66, such as the one or more carbon fiber plies 66a, of the plurality of stacked plies 64, such as the plurality of stacked carbon fiber plies 64a, that are stacked over the one or more fiber distortion initiators 90. In turn, this creates the controlled and repeatable out-of-plane fiber distortion 12b (see FIG. 1) in the composite laminate 14, used for testing purposes 158 (see FIG. 1) and/or process improvement 160 (see FIG. 1).

Each pressure differential region 114 (see FIG. 1) in the composite laminate 14 (see FIG. 1) created by a fiber distortion initiator 90 (see FIG. 1) includes the low pressure (LP) area 116 (see FIG. 1) next to the high pressure (HP) area 118 (see FIG. 1). The pressure in the low pressure area 116 and the pressure in the high pressure area 118 may depend on the composite material 70 (see FIG. 1) used for the composite laminate 14, and may depend on the height 86 (see FIGS. 2B, 2C) created by the one or more fiber distortion initiators 90.

As shown in FIG. 1, the pressurized cure process 140 takes place at an effective pressure 141 and an effective temperature 142, where the effective pressure 141 and the effective temperature 142 are chosen based on the composite material 70 used to make the composite laminate 14, as well as other process considerations and factors. The pressurized cure process 140 takes place for a suitable period of time depending on the effective pressure 141 and the effective temperature 142 chosen. As shown in FIG. 1, the pressurized cure process 140 further comprises the vacuum compaction 144 of the composite laminate 14 with a vacuum system 145 having a vacuum apparatus 146. The vacuum system 145 may include, for example, a vacuum bagging assembly with a vacuum bag film and one or more additional film layers, breather layers, and/or sealants; a vacuum pump assembly with one or more vacuum ports, vacuum lines, a vacuum pump, control valves, and controls; and other suitable vacuum system parts and components known in the art of vacuum bagging composite laminates and other composite structures.

As used herein, "curing" or "cure" means heating the composite laminate 14 up to an effective temperature 142, depending on the cure cycle, applying an effective pressure 141 on the composite laminate 14, and using vacuum compaction 144 with the vacuum system 145 at the effective pressure 141 and the effective temperature 142, on the test system 10, by pulling a vacuum on the plurality of stacked plies 64 having bulk portions 74, such as air 74a, in between the plies 66, to extract the bulk portions 74, such as the air 74a, to compact the plies 66, to create excess material 150 (see FIG. 1) in one or more locations 92 (see FIG. 1), and to create out-of-plane fiber distortion 12a (see FIG. 1), thus obtaining controlled and repeatable out-of-plane fiber distortion 12b (see FIG. 1) in the composite laminate 14 that is cured, as part of the test system 10. The heat at the effective temperature 142 during curing or cure makes the composite material 70 of the plies 66 of the composite laminate 14 soft and viscous, and the vacuum that is pulled on the composite laminate 14 extracts out the air 74a and compacts the composite laminate 14 and the test system 10.

When the plies 66 (see FIG. 1), such as the carbon fiber plies 66a (see FIG. 1), are laid up on the layup tool 20 (see FIG. 1), the plies 66, such as the carbon fiber plies 66a, are laid up with the bulk portions 74 (see FIG. 1), such as air 74a (see FIG. 1), or air pockets, between the plies 66, such as the carbon fiber plies 66a. When using the curved layup tool 20a (see FIGS. 1, 4), this bulk phenomenon creates a radius of curvature 23 (see FIG. 1) that is larger for the layup of the top-most plies 66e (see FIGS. 1, 2B, 2C) at the top of the composite laminate 14, as compared to a radius of curvature 23 of the first ply 66b (see FIGS. 1, 2B, 2C), or bottom ply, that is in contact with the layup surface 26 (see FIGS. 1, 2B) of the curved layup tool 20a. When a vacuum, such as through vacuum compaction 144 (see FIG. 1), is pulled on the composite laminate 14, with the two caul plates 120 (see FIG. 1), or more than two caul plates 120, on top of the plies 66 of the composite laminate 14 for compaction, the bulk portions 74 (see FIG. 1), such as air 74a (see FIG. 1), or air pockets, are extracted from the composite laminate 14, and the last ply 66c (see FIG. 2B), or top ply, may end up having a ply length 67 (see FIG. 1) that is longer than a ply length 67 of the first ply 66b, or bottom ply, due to a radius of curvature 23 (see FIG. 1) that is larger for the last ply 66c than a radius of curvature 23 of the first ply 66b. This creates excess material 150 (see FIG. 1) in plies 66, such as the top-most plies 66e, that are spaced upwardly from the first ply 66b, which is in contact with the layup surface 26 of the curved layup tool 20a.

In addition, when a vacuum, such as through vacuum compaction 144, is pulled or performed on the composite laminate 14 with the two caul plates 120 (see FIGS. 1, 3D), or more than two caul plates 120, on top of the plies 66 (see FIGS. 1, 2B) of the composite laminate 14 for compaction, the plurality of fairing bars 40, such as the first fairing bar 40a and the second fairing bar 40b, restrict or constrain peripheral ends 78 (see FIG. 3C) of the composite laminate 14 (see FIGS. 1, 3C) from expanding outwardly. Thus, the plies 66 of the composite laminate 14 experience a restricted outward expansion 148 (see FIG. 1) due to the placement of the plurality of fairing bars 40 opposite each other and abutting two or more peripheral ends 78 (see FIG. 3C) of the composite laminate 14. Excess material 150 (see FIG. 1) in the top-most plies 66e (see FIG. 1) and in other plies 66 throughout a thickness 84 (see FIG. 3C) of the composite laminate 14 have nowhere to go and thus form fiber distortion 12 (see FIG. 1), such as out-of-plane fiber distortion 12a (see FIG. 1), comprising distorted out-of-plane fibers 110 (see FIG. 1), such as wrinkles 110a (see FIG. 1), with out-of-plane portions 112 (see FIG. 1), that are contained within the composite laminate 14.

In addition to the use of the plurality of fairing bars 40, such as the first fairing bar 40a and the second fairing bar 40b, the fiber distortion 12 (see FIG. 1), such as out-of-plane fiber distortion 12a, may be further controlled by placing one or more of the fiber distortion initiators 90 (see FIG. 1) at one or more locations 92 (see FIG. 1) in the composite laminate 14, to create one or more pressure differential regions 114 (see FIG. 1) of low pressure areas 116 next to and high pressure areas 118, with the pressurized cure process 140. Excess material 150 during vacuum compaction 144 due to the bulk portions 74, such as air 74a, tends to collect around each of the one or more fiber distortion initiators 90.

Figure 2C:
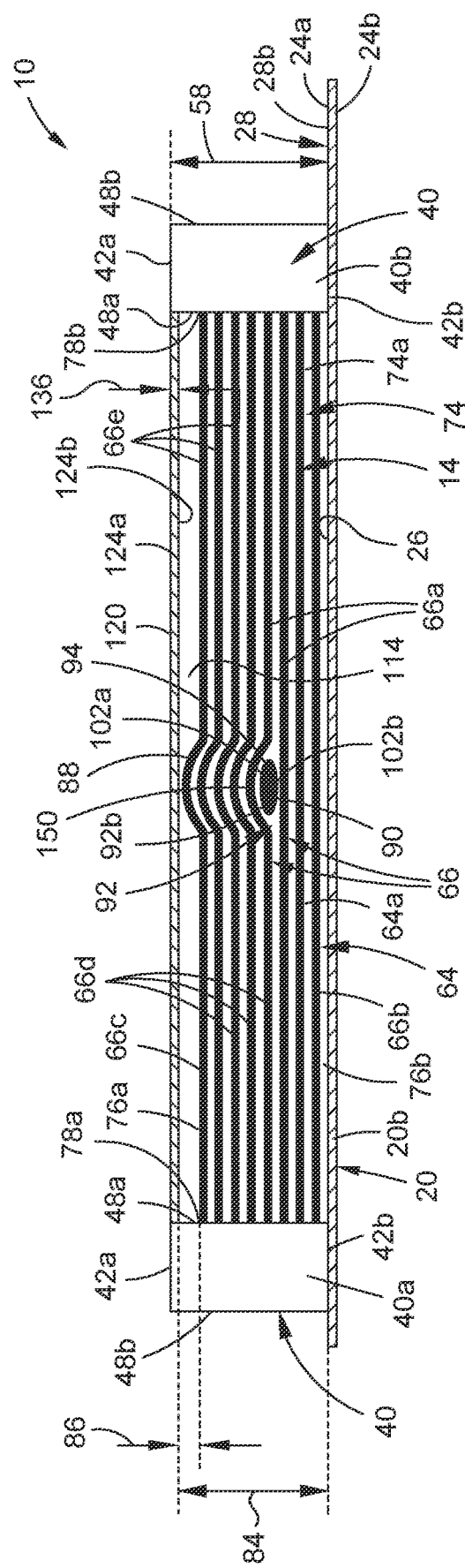
FIG. 2C is an illustration of a front cross-sectional view of another version of a test system of the disclosure with a fiber distortion initiator positioned between two plies of a plurality of stacked plies.

Now referring to FIGS. 2A-2C, FIG. 2A is an illustration of a front cross-sectional view of a layup setup 11 showing only a composite laminate 14 laid up on a layup tool 20, fairing bars 40, and a caul plate 120, but having no fiber distortion initiators 90 added. FIG. 2B is an illustration of a front cross-sectional view of a version of a test system 10 of the disclosure with a fiber distortion initiator 90 positioned between the layup tool 20 and the first ply 66 of the plurality of stacked plies 64. FIG. 2C is an illustration of a front cross-sectional view of another version of a test system 10 of the disclosure with a fiber distortion initiator 90 positioned between two plies 66 of the plurality of stacked plies 64.

As shown in FIGS. 2A-2C, the composite laminate 14 is laid up on the layup surface 26 of the layup tool 20, such as a flat layup tool 20b, having a profile 28, such as a linear profile 28b. The layup tool 20 has a top side 24a (see FIGS. 2A-2C) and a bottom side 24b (see FIGS. 2A-2C).

As further shown in FIGS. 2A-2C, the composite laminate 14 comprises the plurality of stacked plies 64, such as the plurality of stacked carbon fiber plies 64a. As further shown in FIGS. 2A-2C, the plies 66, such as the carbon fiber plies 66a, include the first ply 66b, or bottom ply, positioned over the layup surface 26, the last ply 66c, or top ply, the intermediate plies 66d between the first ply 66b and the last ply 66c, and the top-most plies 66e (see FIGS. 2B, 2C). The composite laminate 14 further comprises the bulk portions 74 (see FIGS. 2A-2C), such as air 74a (see FIGS. 2A-2C), or air pockets, between the plies 66. FIGS. 2A-2C further show a top side 76a, a bottom side 76b, a first peripheral end 78a, and a second peripheral end 78b, of the composite laminate 14. FIGS. 2A-2C further show a thickness 84, or height, of the composite laminate 14.

FIGS. 2A-2C show the composite laminate 14 positioned between two fairing bars 40, including the first fairing bar 40a and the second fairing bar 40b. As shown in FIGS. 2A-2C, each fairing bar 40 has a top side 42a, a bottom side 42b, an inner side end 48a, an outer side end 48b, and a thickness 58, or height. As shown in FIGS. 2A-2C, the first peripheral end 78a of the composite laminate 14 abuts the inner side end 48*a* of the first fairing bar 40*a*, and the second peripheral end 78*b* of the composite laminate 14 abuts the inner side end 48*a* of the second fairing bar 40*b*.

FIGS. 2A-2C show the caul plate 120 positioned over the top side 76*a* of the composite laminate 14 and positioned between the first fairing bar 40*a* and the second fairing bar 40*b*. As shown in FIGS. 2A-2C, the caul plate 120 has a top side 124*a*, and a bottom side 124*b* adjacent the top side 76*a* of the composite laminate 14 and adjacent the last ply 66*c* of the composite laminate 14. The caul plate 120 further has a thickness 136 (see FIGS. 2A-2C).

FIG. 2B shows the fiber distortion initiator 90 positioned on the layup surface 26 of the layup tool 20 and positioned between the layup tool 20 and the first ply 66*b* of the plurality of stacked plies 64 of the composite laminate 14. As shown in FIG. 2B, the fiber distortion initiator 90 is positioned at the location 92 comprising the layup surface location 92*a* under the composite laminate 14. The fiber distortion initiator 90 has a top side 102*a* (see FIG. 2B) and a bottom side 102*b* (see FIG. 2B), and the fiber distortion initiator 90 creates a pressure differential region 114 (see FIG. 2B), as the test system 10 undergoes the pressurized cure process 140 (see FIG. 1). As shown in FIG. 2B, the fiber distortion initiator 90 increases the height 86 of the portion 88 of the one or more plies 66 of the plurality of stacked plies 64, that are stacked over the fiber distortion initiator 90. As further shown in FIG. 2B, excess material 150 collects around the fiber distortion initiator 90, as the test system 10 undergoes the pressurized cure process 140 (see FIG. 1) and vacuum compaction 144 (see FIG. 1).

FIG. 2C shows the fiber distortion initiator 90 positioned between two plies 66, such as intermediate plies 66*d*, of the plurality of stacked plies 64. As shown in FIG. 2C, the fiber distortion initiator 90 is positioned at the location 92 comprising the inter-ply location 92*b* in the composite laminate 14. The fiber distortion initiator 90 has a structure 94 (see FIG. 2C), a top side 102*a* (see FIG. 2C), and a bottom side 102*b* (see FIG. 2C), and the fiber distortion initiator 90 creates the pressure differential region 114 (see FIG. 2C), as the test system 10 undergoes the pressurized cure process 140 (see FIG. 1). As shown in FIG. 2C, the fiber distortion initiator 90 increases the height 86 of the portion 88 of the one or more plies 66 of the plurality of stacked plies 64 stacked over the fiber distortion initiator 90. As further shown in FIG. 2C, excess material 150 collects around the fiber distortion initiator 90, as the test system 10 undergoes the pressurized cure process 140 (see FIG. 1) and vacuum compaction 144 (see FIG. 1).

Figure 3A:
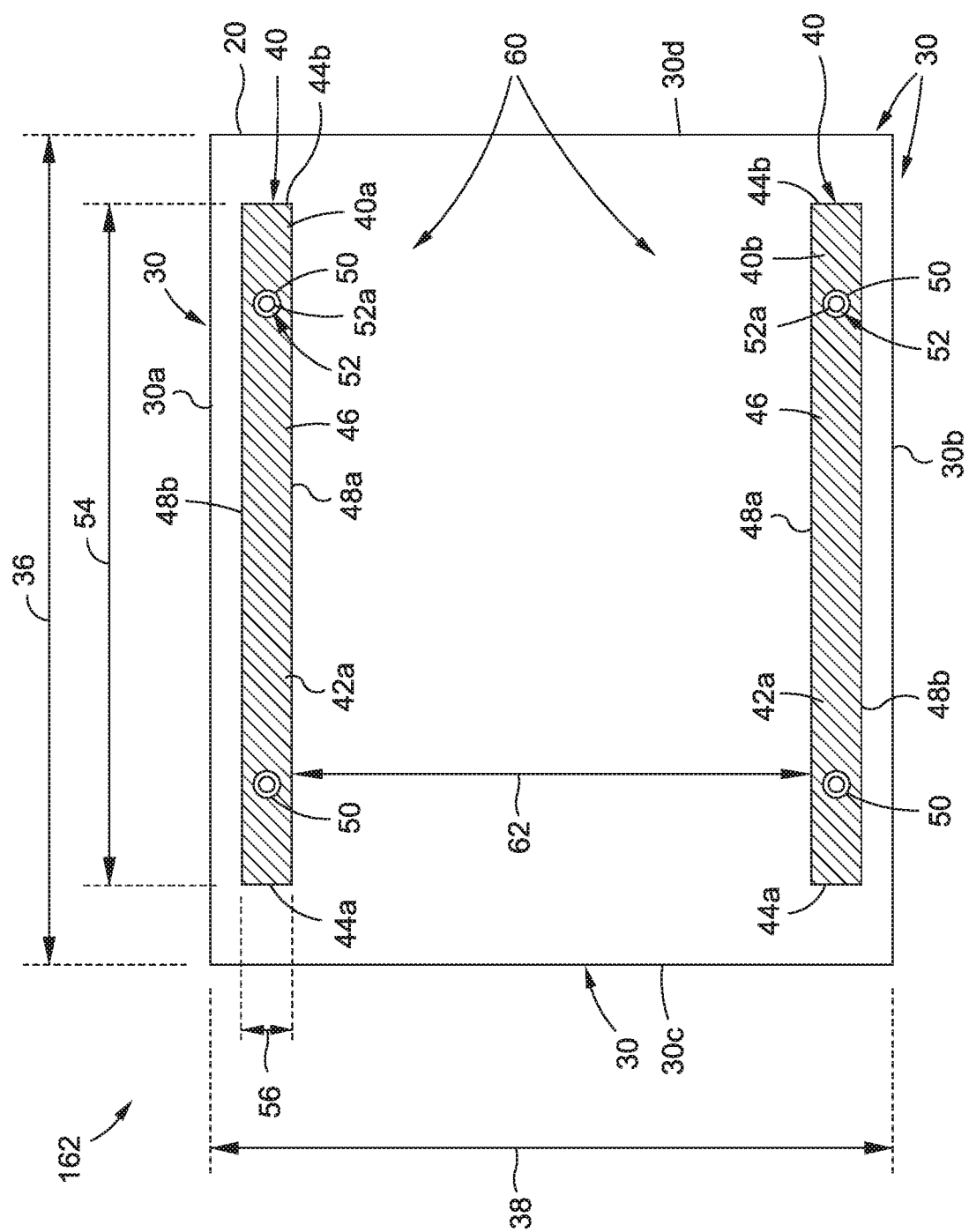
FIG. 3A is an illustration of a top view of a layup tool and two fairing bars, of the test system of the disclosure.

Now referring to FIGS. 3A-3D, FIGS. 3A-3D show various fabrication steps 162-168 for assembling or making an exemplary version of the test system 10 (see FIG. 1). FIG. 3A is an illustration of a top view of the layup tool 20 and two fairing bars 40, of the test system 10 (see FIG. 1) of the disclosure. As shown in FIG. 3A, in a first fabrication step 162 of assembling or making the test system 10 (see FIG. 1), two fairing bars 40, including the first fairing bar 40*a* and the second fairing bar 40*b*, are attached to a top side 24*a* (see FIG. 3B) of the layup tool 20. As shown in FIG. 3A, the first fairing bar 40*a* is positioned opposite the second fairing bar 40*b*, and the first fairing bar 40*a* and the second fairing bar 40*b* are positioned in a spaced arrangement 60 and in a parallel alignment 62 on the layup tool 20.

As further shown in FIG. 3A, the fairing bars 40 have through openings 50. Each through opening 50 (see FIG. 3A) is configured or designed to receive an attachment element 52, such as a fastener 52*a*, for example, a bolt, so that the fairing bar 40 may be securely attached to the layup tool 20. Although FIG. 3A shows each fairing bar 40 having two through openings 50, the fairing bars 40 may have more than two through openings. Preferably, the fairing bars 40 are removably attached to the layup tool 20.

As further shown in FIG. 3A, each fairing bar 40 has a top side 42*a*, a first end 44*a*, a second end 44*b*, a body 46 formed between the first end 44*a* and the second end 44*b*, an inner side end 48*a*, and an outer side end 48*b*. As further shown in FIG. 3A, each fairing bar 40 has a length 54 and a width 56. As further shown in FIG. 3A, the layup tool 20 comprises layup tool ends 30, including a first layup tool end 30*a*, a second layup tool end 30*b*, a third layup tool end 30*c*, and a fourth layup tool end 30*d*. FIG. 3A further shows a length 36 and a width 38 of the layup tool 20.

Figure 3B:
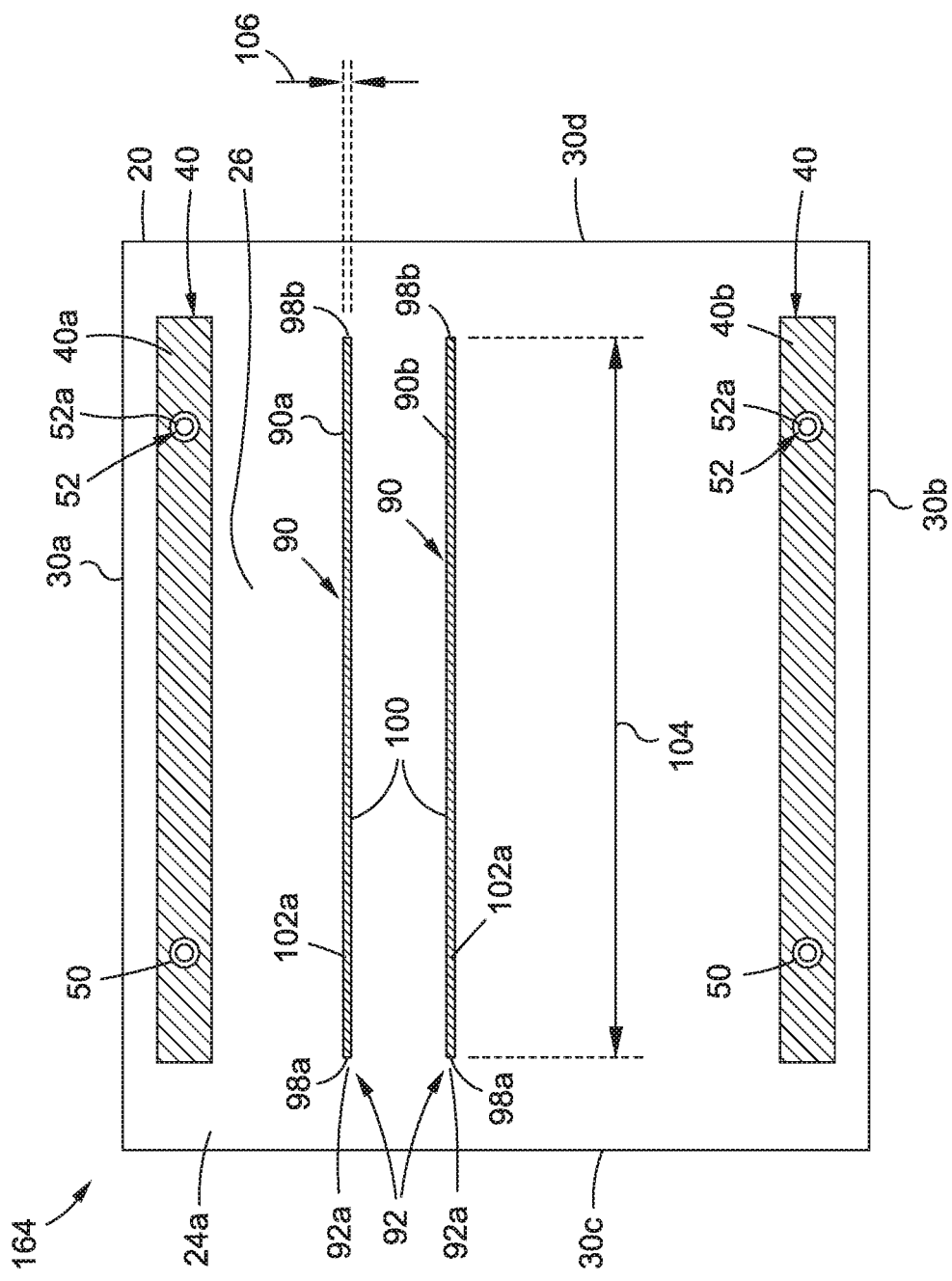
FIG. 3B is an illustration of a top view of the layup tool and two fairing bars of FIG. 3A, with two fiber distortion initiators positioned on the layup tool.

Now referring to FIG. 3B, FIG. 3B is an illustration of a top view of the layup tool 20 and the two fairing bars 40, such as the first fairing bar 40*a* and the second fairing bar 40*b*, of FIG. 3A, with two fiber distortion initiators 90 positioned on the layup tool 20. As shown in FIG. 3B, in a second fabrication step 164 of assembling or making the test system 10 (see FIG. 1), two fiber distortion initiators 90, including a first fiber distortion initiator 90*a* and a second fiber distortion initiator 90*b* are coupled, or laid up on, the layup surface 26 on the top side 24*a* of the layup tool 20. As shown in FIG. 3B, the first fiber distortion initiator 90*a* is positioned opposite the second fiber distortion initiator 90*b* in parallel alignment. Both the first fiber distortion initiator 90*a* and the second fiber distortion initiator 90*b* are positioned between the fairing bars 40, including the first fairing bar 40*a* and the second fairing bar 40*b*. As shown in FIG. 3B, the first fairing bar 40*a* and the second fairing bar 40*b* are attached to the layup tool 20 with one or more attachment elements 52, in the form of fasteners 52*a*, such as bolts, inserted into through openings 50 formed in the first fairing bar 40*a* and the second fairing bar 40*b*. As further shown in FIG. 3B, the first fiber distortion initiator 90*a* and the second fiber distortion initiator 90*b* are both positioned or laid up at the location 92 comprising the layup surface location 92*a*.

As further shown in FIG. 3B, both the first fiber distortion initiator 90*a* and the second fiber distortion initiator 90*b* have a first end 98*a*, a second end 98*b*, a body 100 formed between the first end 98*a* and the second end 98*b*, a top side 102*a*, and a bottom side 102*b* (see FIGS. 2B, 2C) in contact with the layup surface 26 of the layup tool 20. As further shown in FIG. 3B, both the first fiber distortion initiator 90*a* and the second fiber distortion initiator 90*b* have a length 104 and a width 106. The fiber distortion initiators 90, including the first fiber distortion initiator 90*a* and the second fiber distortion initiator 90*b*, also each have a thickness 108 (see FIG. 1). FIG. 3B further shows the first layup tool end 30*a*, the second layup tool end 30*b*, the third layup tool end 30*c*, and the fourth layup tool end 30*d*.

Figure 3C:
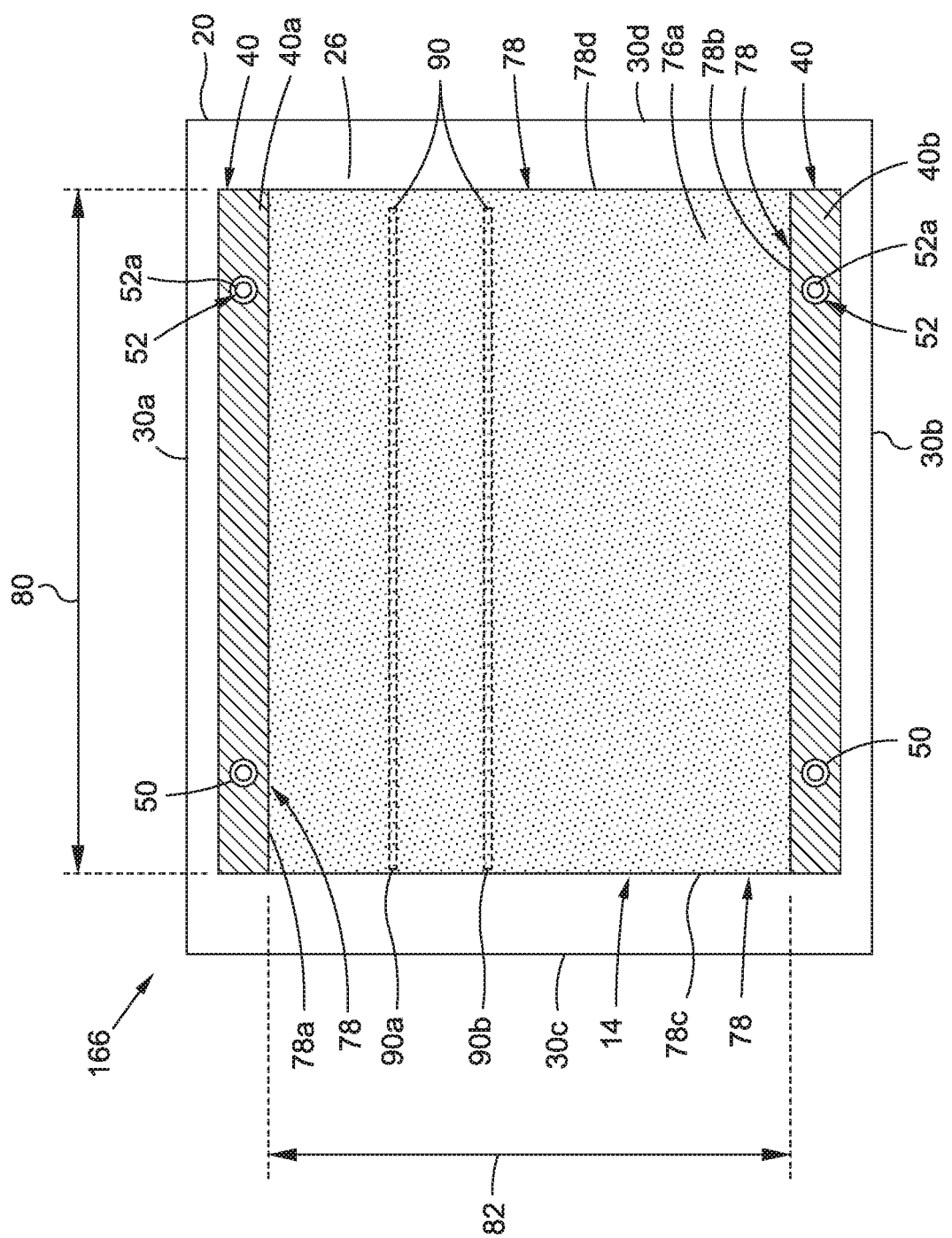
FIG. 3C is an illustration of a top view of the layup tool, the two fairing bars, and the two fiber distortion initiators of FIG. 3B, with a composite laminate positioned between the two fairing bars and laid over the two fiber distortion initiators.

Now referring to FIG. 3C, FIG. 3C is an illustration of a top view of the layup tool 20, the two fairing bars 40, such as the first fairing bar 40*a* and the second fairing bar 40*b*, and the two fiber distortion initiators 90, such as the first fiber distortion initiator 90*a* and the second fiber distortion initiator 90*b*, of FIG. 3B, with the composite laminate 14 positioned between the two fairing bars 40 and laid over the two fiber distortion initiators 90.

As shown in FIG. 3C, in a third fabrication step 166 of assembling or making the test system 10 (see FIG. 1), the composite laminate 14 is laid up on the layup surface 26 of the top side 24*a* of the layup tool 20 over the two fiber distortion initiators 90, including the first fiber distortion initiator 90*a* and the second fiber distortion initiator 90*b*. As shown in FIG. 3C, the composite laminate 14 is positioned between, and adjacent to, the first fairing bar 40a and the second fairing bar 40b, respectively.

As shown in FIG. 3C, the composite laminate 14 has a top side 76a, a bottom side 76b (see FIGS. 2A-2C), and peripheral ends 78, including a first peripheral end 78a, a second peripheral end 78b, a third peripheral end 78c, and a fourth peripheral end 78d. As further shown in FIG. 3C, the composite laminate 14 has a length 80 and a width 82. As shown in FIG. 3C, the first peripheral end 78a of the composite laminate 14 abuts, and is adjacent to, the inner side end 48a (see FIG. 3A) of the first fairing bar 40a, and the second peripheral end 78b of the composite laminate 14 abuts, and is adjacent to, the inner side end 48a (see FIG. 3A) of the second fairing bar 40b. As shown in FIG. 3C, the first fairing bar 40a and the second fairing bar 40b are attached to the layup tool 20 with one or more attachment elements 52, in the form of fasteners 52a, such as bolts, inserted into through openings 50 formed in the fairing bars 40. As further shown in FIG. 3C, the first fiber distortion initiator 90a and the second fiber distortion initiator 90b are positioned under the composite laminate 14. FIG. 3C further shows the first layup tool end 30a, the second layup tool end 30b, the third layup tool end 30c, and the fourth layup tool end 30d.

Figure 3D:
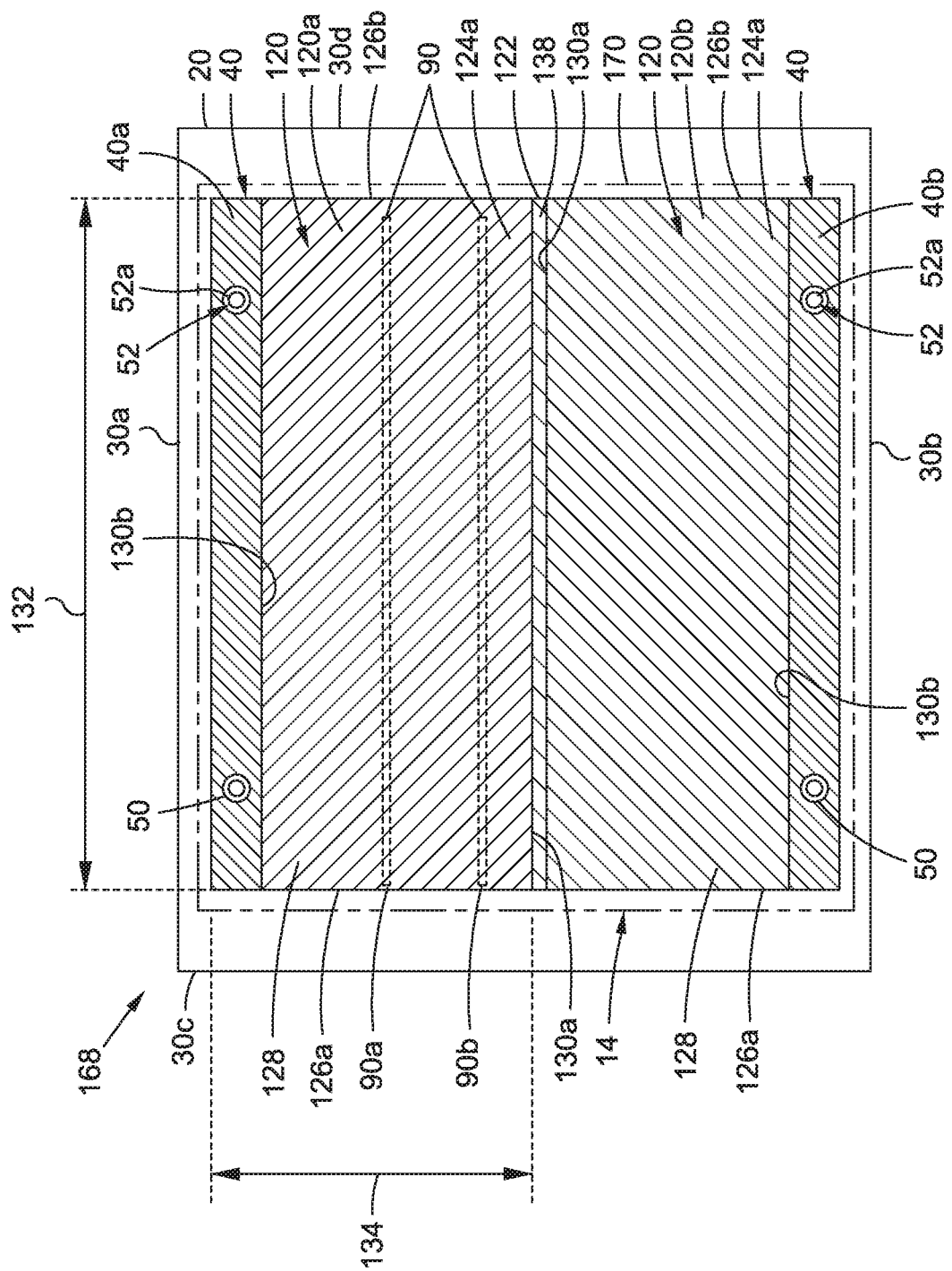
FIG. 3D is an illustration of a top view of the layup tool, the two fairing bars, the two fiber distortion initiators, and the composite laminate of FIG. 3C, with two caul plates having a gap in between them and positioned between the two fairing bars and laid over the composite laminate.

Now referring to FIG. 3D, FIG. 3D is an illustration of a top view of the layup tool 20, the two fairing bars 40, such as the first fairing bar 40a and the second fairing bar 40b, the two fiber distortion initiators 90, such as the first fiber distortion initiator 90a and the second fiber distortion initiator 90b, and the composite laminate 14, of FIG. 3C, with two caul plates 120, in the form of a first caul plate 120a and a second caul plate 120b, with a gap 122 in between the first caul plate 120a and the second caul plate 120b, and the two caul plates 120 positioned between the two fairing bars 40 and laid substantially over the top side 76a (see FIG. 3C) of the composite laminate 14.

As shown in FIG. 3D, in a fourth fabrication step 168 of assembling or making the test system 10 (see FIG. 1), the first caul plate 120a and the second caul plate 120b are placed or positioned over the composite laminate 14, of FIG. 3C, and spaced apart or gapped with respect to each other, with the gap 122 present in between the first caul plate 120a and the second caul plate 120b, prior to the pressurized cure process 140 (see FIG. 1). As shown in FIG. 3D, the first caul plate 120a and the second caul plate 120b are positioned between, and adjacent to, the first fairing bar 40a and the second fairing bar 40b.

As further shown in FIG. 3D, each caul plate 120 includes a top side 124a, a bottom side 124b (see FIGS. 2A-2C), a first end 126a, a second end 126b, a body 128 formed between the first end 126a and the second end 126b, an inner side end 130a, an outer side end 130b, a length 132, and a width 134. As shown in FIG. 3D, the outer side end 130b of the first caul plate 120a abuts, and is adjacent to, the inner side end 48a (see FIG. 3A) of the first fairing bar 40a, and the outer side end 130b of the second caul plate 120b abuts, and is adjacent to, the inner side end 48a (see FIG. 3A) of the second fairing bar 40b. As further shown in FIG. 3D, a surfacer layer 138 may optionally be added between the composite laminate 14 and the first caul plate 120a and the second caul plate 120b. The surfacer layer 138 (see FIG. 3D) is shown through the gap 122 between the first caul plate 120a and the second caul plate 120b.

As shown in FIG. 3D, the first fairing bar 40a and the second fairing bar 40b are attached to the layup tool 20 with one or more attachment elements 52, in the form of fasteners 52a, such as bolts, inserted into through openings 50 formed in the fairing bars 40. As further shown in FIG. 3D, the first fiber distortion initiator 90a and the second fiber distortion initiator 90b are also positioned under the first caul plate 120a and the second caul plate 120b. FIG. 3C further shows the first layup tool end 30a, the second layup tool end 30b, the third layup tool end 30c, and the fourth layup tool end 30d. FIG. 3D further shows the composite laminate 14 comprising an uncured part 170, prior to the composite laminate 14 undergoing the pressurized cure process 140 (see FIG. 1).

Figure 4:
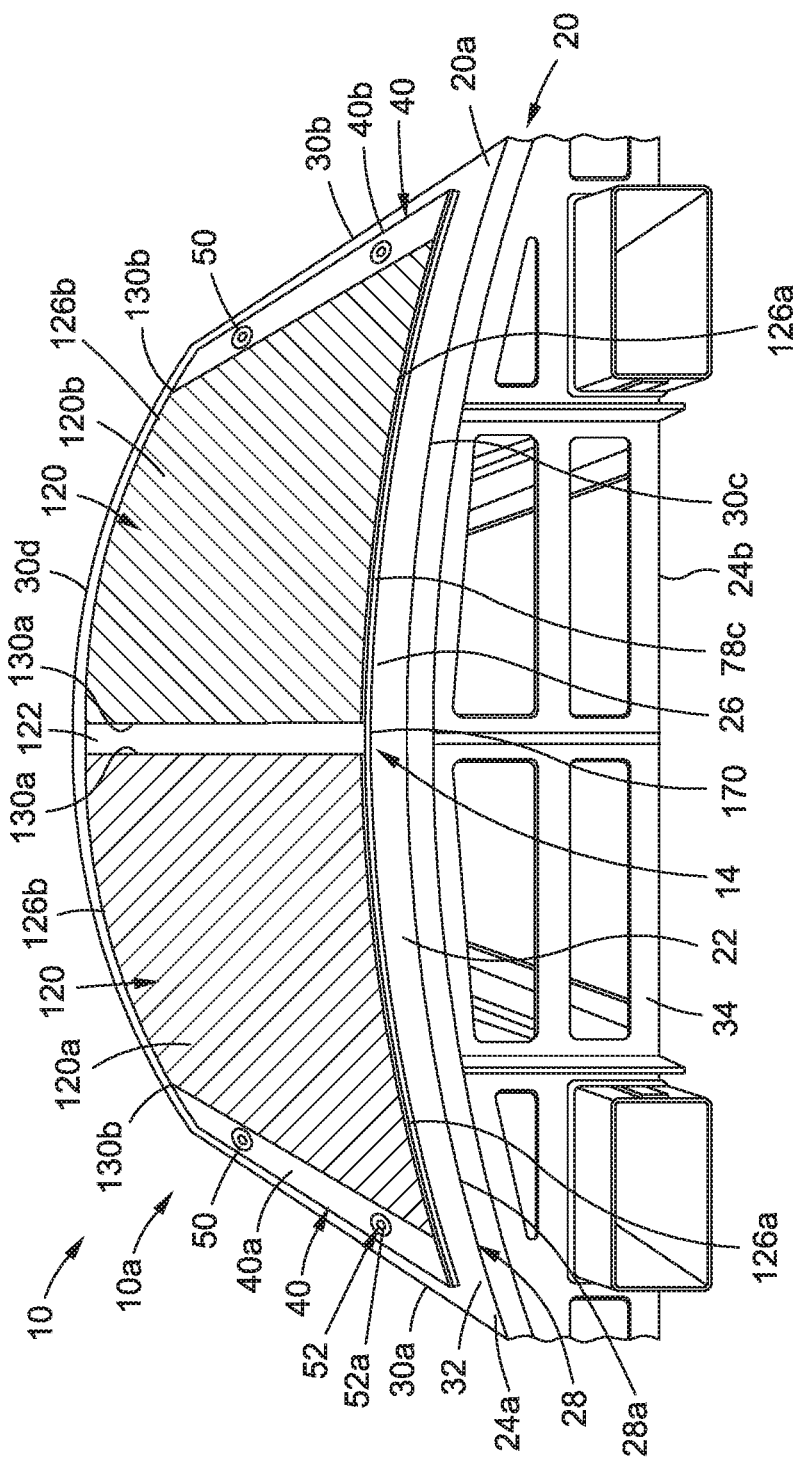
FIG. 4 is an illustration of a front perspective view of an exemplary version of a test system of the disclosure.

Now referring to FIG. 4, FIG. 4 is an illustration of a front perspective view of an exemplary version of a test system 10, such as in the form of a sub-scale test system 10a, of the disclosure, where the layup tool 20 comprises a curved layup tool 20a. As shown in FIG. 4, the layup tool 20, such as in the form of curved layup tool 20a, comprises a layup portion 32 coupled to a base structure portion 34, to form, for example, a test bed. As further shown in FIG. 4, the layup tool 20, such as in the form of curved layup tool 20a, comprises a top side 24a, a bottom side 24b, and a layup surface 26 on the top side 24a. As further shown in FIG. 4, the layup surface 26 of the layup tool 20 has a curved configuration 22 and a profile 28 comprising a convex profile 28a. FIG. 4 further shows the first layup tool end 30a opposite the second layup tool end 30b, and the third layup tool end 30c opposite the fourth layup tool end 30d.

As further shown in FIG. 4, the test system 10, such as in the form of sub-scale test system 10a, comprises two fairing bars 40, including the first fairing bar 40a and the second fairing bar 40b, both attached to the top side 24a of the layup tool 20, via attachment elements 52, such as fasteners 52a, inserted into through openings 50 formed in the two fairing bars 40. As shown in FIG. 4, the first fairing bar 40a is positioned opposite the second fairing bar 40b, and the first fairing bar 40a and the second fairing bar 40b are preferably positioned in a spaced arrangement 60 (see FIG. 1) and in a parallel alignment 62 (see FIG. 1) on the layup tool 20. Preferably, the fairing bars 40 are removably attached to the layup tool 20.

As further shown in FIG. 4, the test system 10, such as in the form of sub-scale test system 10a, comprises the composite laminate 14 laid over one or more fiber distortion initiators 90 (not shown, but see FIGS. 1, 3B). The one or more fiber distortion initiators 90 are positioned at one or more locations 92 (see FIGS. 1, 2B, 2C) under, and adjacent to, one or more plies 66 (see FIGS. 1, 2B, 2C) of the plurality of stacked plies 64 (see FIGS. 1, 2B, 2C), and each of the one or more fiber distortion initiators 90 comprises a structure 94 (see FIG. 1) having a volume 96 (see FIG. 1) that increases the height 86 (see FIGS. 2B, 2C) of the portion 88 (see FIGS. 2B, 2C) of the one or more plies 66 of the plurality of stacked plies 64 that are stacked over each of the one or more fiber distortion initiators 90.

As further shown in FIG. 4, two caul plates 120, in the form of the first caul plate 120a and the second caul plate 120b, with the gap 122 in between the first caul plate 120a and the second caul plate 120b, are positioned between the two fairing bars 40 and laid over the composite laminate 14. FIG. 4 shows the third peripheral end 78c of the composite laminate 14. FIG. 4 further shows the first end 126a, the second end 126b, the inner side end 130a, and the outer side end 130b of each of the first caul plate 120a and the second caul plate 120b. As shown in FIG. 4, the first caul plate 120a and the second caul plate 120b are positioned between, and adjacent to, the first fairing bar 40a and the second fairing bar 40b, and the first caul plate 120a and the second caul plate 120b are positioned next to each other, and gapped with respect to each other, with the gap 122 present between the first caul plate 120a and the second caul plate 120b.

As shown in FIG. 4, the outer side end 130b of the first caul plate 120a abuts, and is adjacent to, the inner side end 48a (see FIG. 3A) of the first fairing bar 40a, and the outer side end 130b of the second caul plate 120b abuts, and is adjacent to, the inner side end 48a (see FIG. 3A) of the second fairing bar 40b. As further shown in FIG. 4, the composite laminate 14 comprises an uncured part 170, prior to the composite laminate 14 undergoing the pressurized cure process 140 (see FIG. 1).

Figure 5A:
FIG. 5A is an illustration of a top view of a cured composite part with distorted out-of-plane fibers.

Now referring to FIG. 5A, FIG. 5A is an illustration of a top view of a cured composite part 172, such as a cured panel 172a, after the test system 10 (see FIGS. 1, 2B, 2C, 4) has undergone the pressurized cure process 140 (see FIG. 1). As shown in FIG. 5A, the cured composite part 172, such as the cured panel 172a, includes distorted out-of-plane fibers 110, such as wrinkles 110a. As further shown in FIG. 5A, the distorted out-of-plane fibers 110, such as wrinkles 110a, may be created or formed in one or more controlled locations 156 with the test system 10 (see FIG. 1) of the disclosure. The cured composite part 172, such as the cured panel 172a, may be divided into test coupons for further testing, if desired.

Figure 5B:
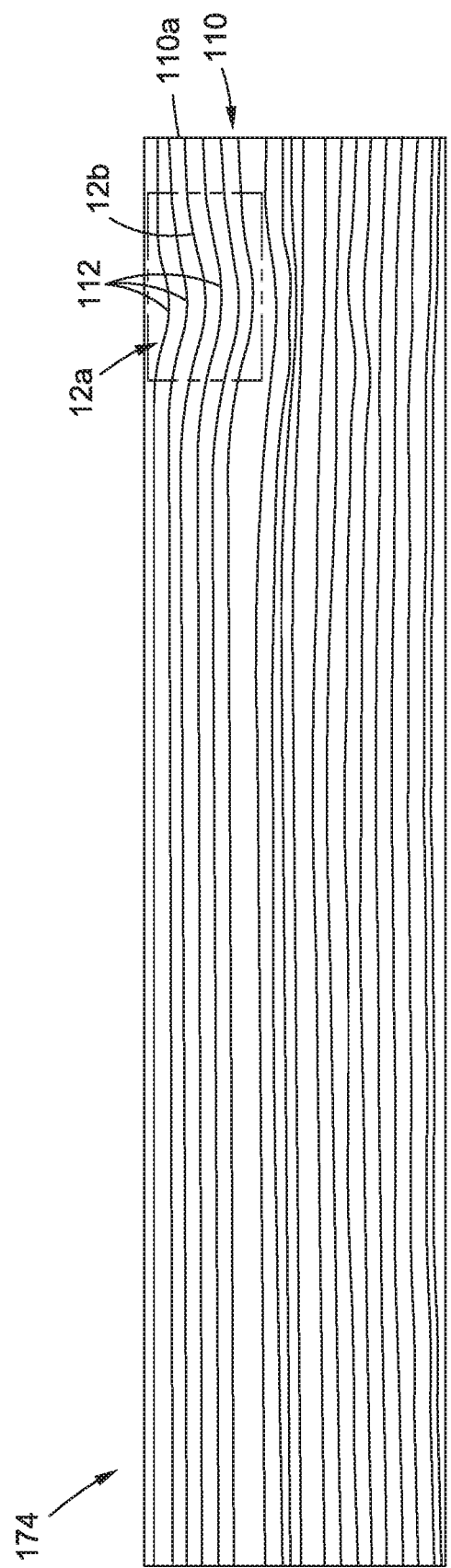
FIG. 5B is an illustration of a cross-sectional scan of the distorted out-of-plane fibers of circle 5B of FIG. 5A.

Now referring to FIG. 5B, FIG. 5B is an illustration of a cross-sectional scan 174 of the distorted out-of-plane fiber 110, such as the wrinkle 110a, of circle 5B of FIG. 5A. The cross-sectional scan 174 was created using destructive analysis, by taking a picture of the edge of a cross-section that was physically cut out of the composite laminate 14 that was cured with the pressurized cure process 140. As shown in the cross-sectional scan 174, the distorted out-of-plane fiber 110, such as the wrinkle 110a, has out-of-plane portions 112. FIG. 5B further shows the out-of-plane fiber distortion 12a, resulting in the controlled and repeatable out-of-plane fiber distortion 12b, created using the test system 10 (see FIG. 1) of the disclosure.

Figure 6:
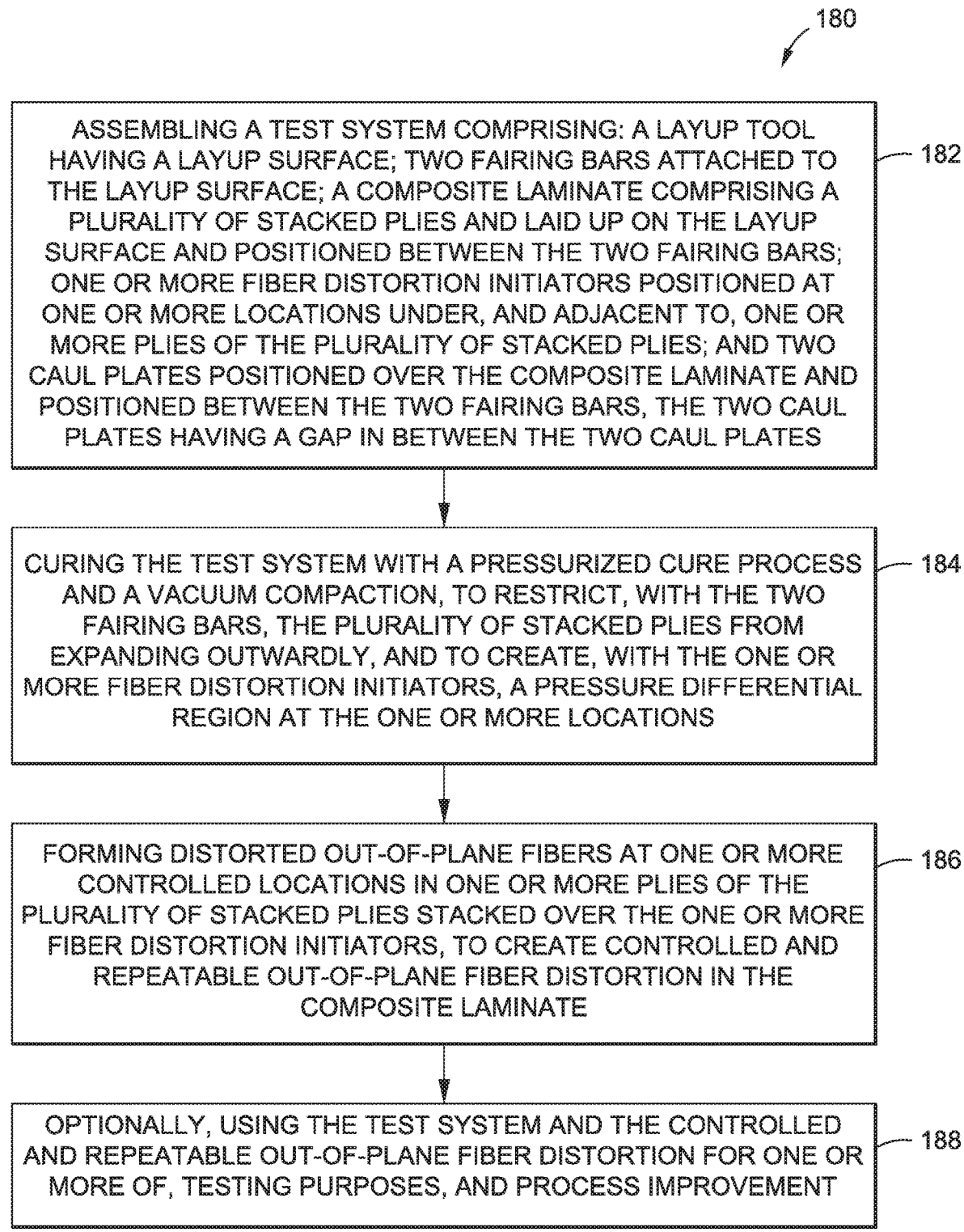
FIG. 6 is an illustration of a flow diagram of an exemplary version of a method of the disclosure.

Now referring to FIG. 6, FIG. 6 is an illustration of a flow diagram of an exemplary version of a method 180 for creating controlled and repeatable out-of-plane fiber distortion 12b (see FIG. 1) in a composite laminate 14 (see FIG. 1) using a version of the test system 10 (see FIG. 1) of the disclosure.

As shown in FIG. 6, the method 180 comprises the step of assembling 182 the test system 10 (see FIG. 1). As discussed in detail above, the test system 10 comprises the layup tool 20 (see FIGS. 1, 3A) having a layup surface 26 (see FIGS. 1, 3B). In one version, the layup tool 20 may comprise the curved layup tool 20a (see FIGS. 1, 4) with the curved configuration 22 (see FIGS. 1, 4) and having a radius of curvature 23 (see FIG. 1). In another version, the layup tool 20 (see FIGS. 1, 2B) may comprise the flat layup tool 20b (see FIGS. 1, 2B). The step of assembling 182 (see FIG. 6) the test system 10 (see FIG. 1) may further comprise assembling 182 the test system 10 with the layup tool 20 (see FIGS. 1, 4) comprising the curved layup tool 20a (see FIGS. 1, 4), and the layup surface 26 (see FIGS. 1, 4) having the convex profile 28a (see FIGS. 1, 4).

As discussed in detail above, the test system 10 further comprises a plurality of fairing bars 40, such as two fairing bars 40 (see FIGS. 1, 2B, 3A), attached to the layup surface 26 and spaced opposite to one another in a spaced arrangement 60 (see FIGS. 1, 3A) and preferably in a parallel alignment 62 (see FIGS. 1, 3A). The two fairing bars 40, such as the first fairing bar 40a (see FIGS. 1, 3A) and the second fairing bar 40b (see FIGS. 1, 3A), are preferably removably attached to the layup surface 26 with one or more attachment elements 52 (see FIGS. 3A, 4), such as one or more fasteners 52a (see FIGS. 3A, 4), for example, bolts. However, other suitable attachment elements 52 may be used to secure the plurality of fairing bars 40 to the layup tool 20.

As discussed in detail above, the test system 10 further comprises the composite laminate 14 (see FIGS. 1, 2B, 3C) comprising the plurality of stacked plies 64 (see FIGS. 1, 2B), such as the plurality of stacked carbon fiber plies 64a (see FIG. 1). The composite laminate 14 is laid up on the layup surface 26 (see FIGS. 1, 2B, 3C) of the layup tool 20 and positioned between the two fairing bars 40, such as the first fairing bar 40a and the second fairing bar 40b.

As discussed in detail above, the test system 10 further comprises one or more fiber distortion initiators 90 (see FIGS. 1, 2B, 3C) positioned at one or more locations 92 (see FIGS. 1, 2B, 3B) under, and adjacent to, one or more plies 66 (see FIGS. 2B, 2C) of the plurality of stacked plies 64 (see FIGS. 2B, 2C). Each of the one or more fiber distortion initiators 90 (see FIG. 1) comprises a structure 94 (see FIG. 1) having a volume 96 (see FIG. 1) that increases the height 86 (see FIGS. 2B, 2C) of a portion 88 (see FIGS. 2B, 2C) of the one or more plies 66 of the plurality of stacked plies 64, that are stacked over each of the one or more fiber distortion initiators 90 (see FIGS. 1, 2B, 2C).

The step of assembling 182 the test system 10 (see FIG. 1) may further comprise assembling 182 the test system 10 with at least one of the one or more fiber distortion initiators 90 (see FIG. 2B) positioned adjacent to, and between, the layup surface 26 (see FIG. 2B) of the layup tool 20 (see FIG. 2B) and the first ply 66a (see FIG. 2B) laid over the layup surface 26 and the at least one fiber distortion initiator 90. The step of assembling 182 the test system 10 may further comprise assembling 182 the test system 10 with at least one of the one or more fiber distortion initiators 90 (see FIG. 2C) positioned adjacent to, and between, two plies 66 (see FIG. 2C) of the plurality of stacked plies 64 (see FIG. 2C).

As discussed in detail above, the test system 10 further comprises two caul plates 120 (see FIGS. 1, 2B, 3D), or caul sheets, positioned over the composite laminate 14 (see FIGS. 1, 2B) and positioned between the two fairing bars 40 (see FIGS. 1, 2B, 3D), such as the first fairing bar 40a and the second fairing bar 40b. The two caul plates 120 (see FIGS. 3D, 4) may comprise the first caul plate 120a (see FIGS. 3D, 4) and the second caul plate 120b (see FIGS. 3D, 4) positioned next to each other with the gap (see FIGS. 3D, 4) present between the inner side ends 130a (see FIGS. 3D, 4) of each of the first caul plate 120a and the second caul plate 120b. The test system 10 may comprise more than two caul plates 120, such as four, six, eight, or another suitable number of caul plates 120, with one or more gaps 122 in between respective caul plates 120.

The step of assembling 182 the test system 10 may further comprise assembling 182 the test system 10 comprising a sub-scale test system 10a (see FIGS. 1, 4) for creating the controlled and repeatable out-of-plane fiber distortion 12b (see FIGS. 1, 5B) at a sub-scale level 16 (see FIG. 1) that is representative of fiber distortion 12 (see FIG. 1), such as out-of-plane fiber distortion 12a (see FIG. 1), of a full-scale size part 18 (see FIG. 1).

As shown in FIG. 6, the method 180 further comprises the step of curing 184 the test system 10 with a pressurized cure process 140 (see FIG. 1) and a vacuum compaction 144 (see FIG. 1), to restrict, with the two fairing bars 40 (see FIGS. 1, 2B, 4), the plurality of stacked plies 64 (see FIGS. 1, 2B) from expanding outwardly, and to create, with the one or more fiber distortion initiators 90 (see FIGS. 1, 2B), a pressure differential region 114 (see FIGS. 1, 2B, 2C) at the one or more locations 92 (see FIGS. 1, 2B, 2C). The pressurized cure process 140 (see FIG. 1) comprises the composite laminate 14 undergoing cure at an effective pressure 141 (see FIG. 1) and an effective temperature 142 (see FIG. 1). The effective pressure 141 and the effective temperature 142 are chosen based on the composite material 70 (see FIG. 1) used to make the composite laminate 14, as well as other process considerations and factors. The pressurized cure process 140 takes place for a suitable period of time depending on the effective pressure 141 and the effective temperature 142 chosen.

The pressurized cure process 140 (see FIG. 1) further comprises the vacuum compaction 144 (see FIG. 1) of the composite laminate 14 using the vacuum system 145 (see FIG. 1) having the vacuum apparatus 146 (see FIG. 1). When the vacuum compaction 144 is pulled or performed on the composite laminate 14 with the two caul plates 120 (see FIGS. 1, 3D) on top of the plies 66 (see FIGS. 1, 2B) of the composite laminate 14 for compaction, and the bulk portions 74 (see FIG. 1), such as air 74a (see FIG. 1), or air pockets, in between the plies 66 are extracted from the composite laminate 14, excess material 150 (see FIG. 1) is created, and in particular, created in the top-most plies 66e, or uppermost plies.

As shown in FIG. 6, the method 180 further comprises the step of forming 186 distorted out-of-plane fibers 110 (see FIGS. 1, 5A), such as wrinkles 110a (see FIGS. 1, 5A), at one or more controlled locations 156 (see FIGS. 1, 5A) in the one or more plies 66 (see FIGS. 1, 2B) of the plurality of stacked plies 64 (see FIGS. 1, 2B), that are stacked over the one or more fiber distortion initiators 90 (see FIGS. 1, 2B, 2C). This creates the controlled and repeatable out-of-plane fiber distortion 12b (see FIGS. 1, 5B) in the composite laminate 14 (see FIGS. 1, 2B).

As shown in FIG. 6, the method 180 may further optionally comprise, after the step of forming 186 the distorted out-of-plane fibers 110, the step of using 188 the test system 10 (see FIGS. 1, 2B, 4) and the controlled and repeatable out-of-plane fiber distortion 12b (see FIG. 1), for one or more of, testing purposes 158 (see FIG. 1), and process improvement 160 (see FIG. 1), for eliminating or minimizing out-of-plane fiber distortion 12a (see FIGS. 1, 5B) in composite structures 218 (see FIG. 7), such as composite laminates 14 (see FIG. 1).

Figure 7:
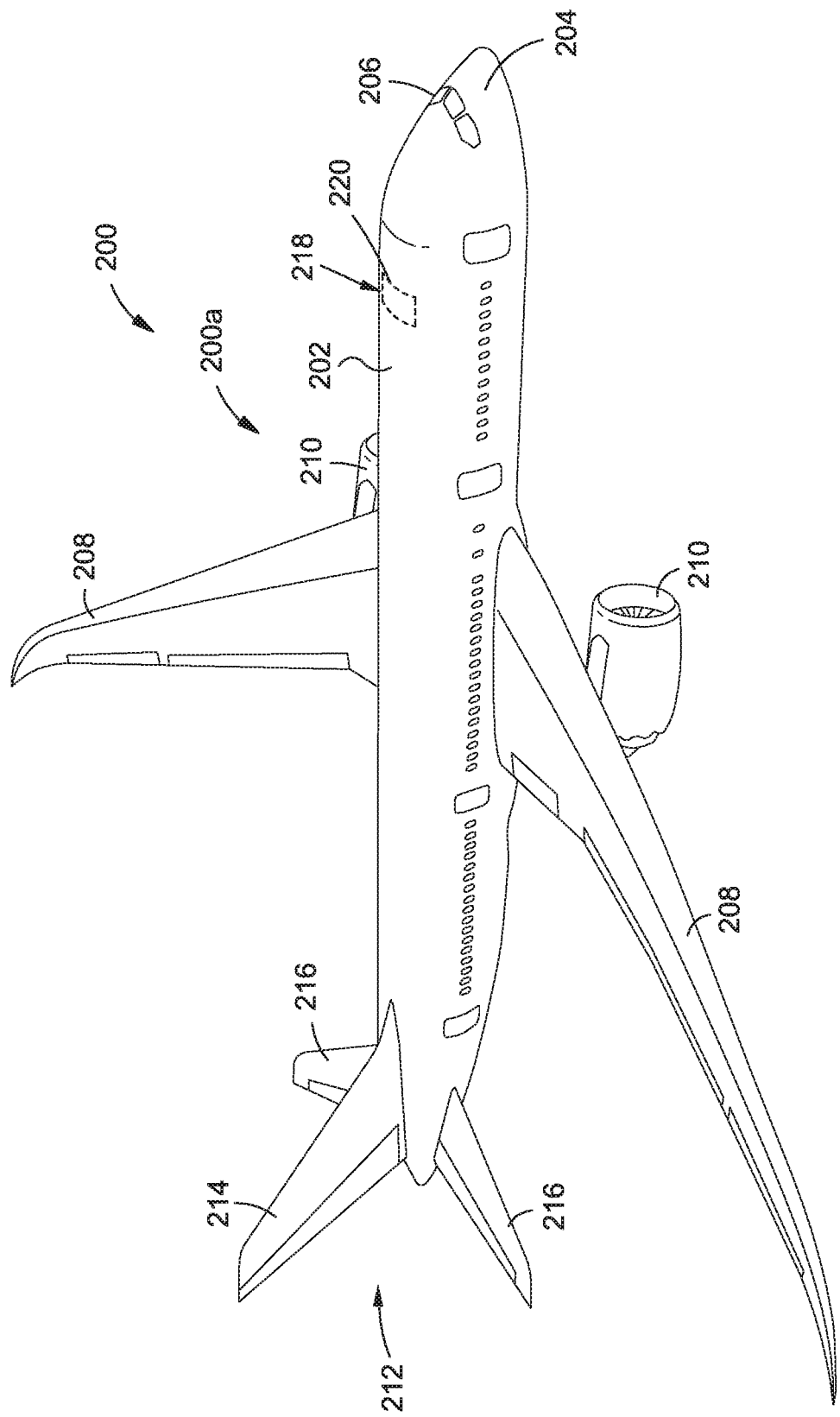
FIG. 7 is an illustration of a perspective view of an aircraft that incorporates an aircraft structure that may be tested on a sub-scale level with a version of a test system of the disclosure.

Now referring to FIG. 7, FIG. 7 is an illustration of a perspective view of an air vehicle 200, such as an aircraft 200a, that incorporates a composite structure 218, such as a fuselage barrel section 220, that may be tested on a sub-scale level 16 (see FIG. 1) with a version of a test system 10 (see FIG. 1) of the disclosure. As shown in FIG. 7, the air vehicle 200, such as the aircraft 200a, comprises a fuselage 202, a nose 204, a cockpit 206, a pair of wings 208 and engines 210, and an empennage 212 comprising a horizontal stabilizer 214 and vertical stabilizers 216.

Figure 8:
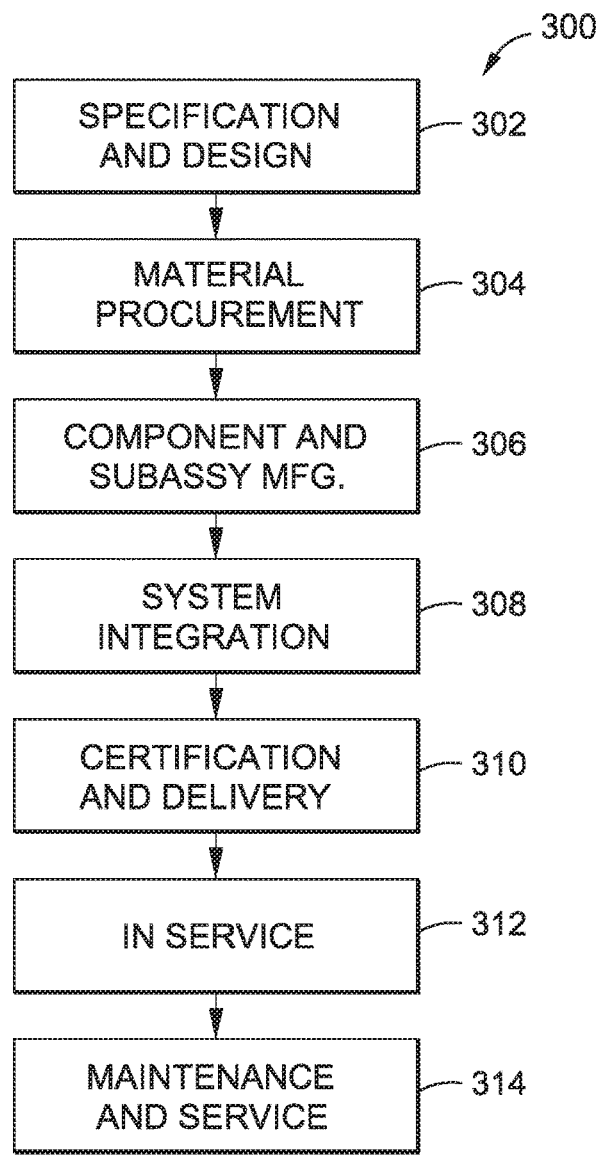
FIG. 8 is an illustration of a flow diagram of a version of an aircraft manufacturing and service method.
Figure 9:
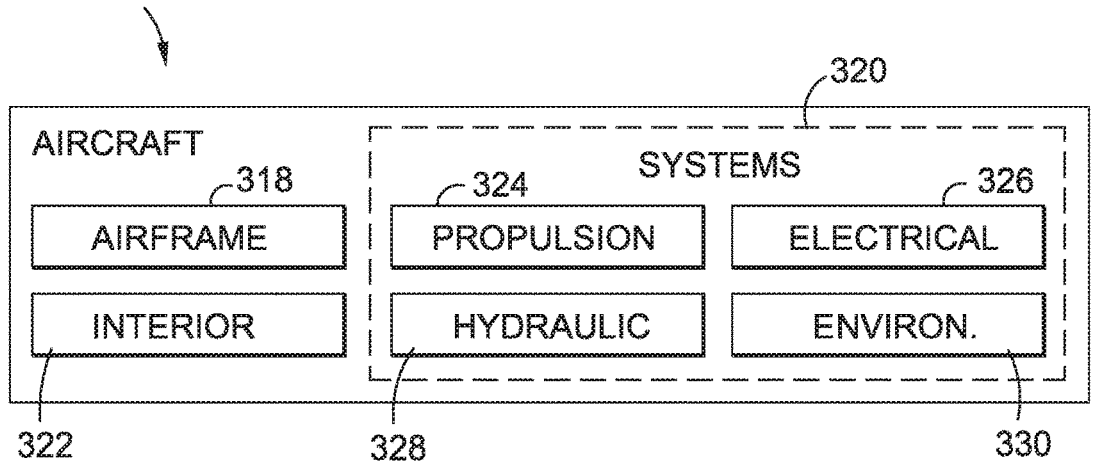
FIG. 9 is an illustration of a functional block diagram of a version of an aircraft.

Now referring to FIGS. 8 and 9, FIG. 8 is an illustration of a flow diagram of an aircraft manufacturing and service method 300, and FIG. 9 is an illustration of a block diagram of an aircraft 316. Referring to FIGS. 8 and 9, versions of the disclosure may be described in the context of the aircraft manufacturing and service method 300 as shown in FIG. 8, and the aircraft 316 as shown in FIG. 9.

During pre-production, exemplary aircraft manufacturing and service method 300 may include specification and design 302 of the aircraft 316 and material procurement 304. During manufacturing, component and subassembly manufacturing 306 and system integration 308 of the aircraft 316 takes place. Thereafter, the aircraft 316 may go through certification and delivery 310 in order to be placed in service 312. While in service 312 by a customer, the aircraft 316 may be scheduled for routine maintenance and service 314 (which may also include modification, reconfiguration, refurbishment, and other suitable services).

Each of the processes of the aircraft manufacturing and service method 300 may be performed or carried out by a system integrator, a third party, and/or an operator (e.g., a customer). For the purposes of this description, a system integrator may include, without limitation, any number of aircraft manufacturers and major-system subcontractors. A third party may include, without limitation, any number of vendors, subcontractors, and suppliers. An operator may include an airline, leasing company, military entity, service organization, and other suitable operators.

As shown in FIG. 9, the aircraft 316 produced by the exemplary aircraft manufacturing and service method 300 may include an airframe 318 with a plurality of systems 320 and an interior 322. Examples of the plurality of systems 320 may include one or more of a propulsion system 324, an electrical system 326, a hydraulic system 328, and an environmental system 330. Any number of other systems may be included. Although an aerospace example is shown, the principles of the disclosure may be applied to other industries, such as the automotive industry.

Methods and systems embodied herein may be employed during any one or more of the stages of the aircraft manufacturing and service method 300. For example, components or subassemblies corresponding to component and subassembly manufacturing 306 may be fabricated or manufactured in a manner similar to components or subassemblies produced while the aircraft 316 is in service 312. Also, one or more apparatus embodiments, method embodiments, or a combination thereof, may be utilized during component and subassembly manufacturing 306 and system integration 308, for example, by substantially expediting assembly of or reducing the cost of the aircraft 316. Similarly, one or more of apparatus embodiments, method embodiments, or a combination thereof, may be utilized while the aircraft 316 is in service 312, for example and without limitation, to maintenance and service 314.

Disclosed embodiments of the test system 10 (see FIGS. 1, 2B, 2C, 4), and method 180 (see FIG. 6) provide for the intentional creation of controlled and repeatable out-of-plane fiber distortion 12b (see FIG. 1) at a sub-scale level 16 (see FIG. 1), that is representative fiber distortion 12c (see FIG. 1) of a full-scale size part 18 (see FIG. 1), for example, a fuselage barrel section 220 (see FIG. 7) of the fuselage 202 (see FIG. 7) of an aircraft 200a (see FIG. 7), or another suitable full-scale size part 18, or structure. The test system 10 (see FIG. 1) facilitates and provides for the intentional creation of distorted out-of-plane fibers 110 (see FIG. 1), or wrinkles 110a (see FIG. 1), in composite structures 218 (see FIG. 7), such as composite laminates 14 (see FIG. 1), and this provides increased repeatability 154 (see FIG. 1) and controlled location 156 (see FIG. 1) of the distorted out-of-plane fibers 110, or wrinkles 110a, in the composite laminate 14. Thus, the test system 10, such as the sub-scale test system 10a, creates the distorted out-of-plane fibers 110, or wrinkles 110a, with increased repeatability 154 on a sub-scale level 16, so that solutions to the problem of formation of distorted out-of-plane fibers 110, or wrinkles 110a, on a full-scale size part 18 can more easily and accurately be solved. The test system 10 and the method 180 create out-of-plane fiber distortion 12a (see FIG. 1) with increased repeatability 154, and the test system 10 and the method 180 are less expensive and costly, less labor intensive, less time intensive, and have a decreased turnaround time, as compared to testing or creating fiber distortion 12 in full-scale size parts 18. Further, the test system 10 and the controlled and repeatable out-of-plane fiber distortion 12b may be used for testing purposes 158 (see FIG. 1) and/or process improvement 160 (see FIG. 1), for example, for finding solutions to eliminate or minimize fiber distortion 12 (see FIG. 1), such as out-of-plane fiber distortion 12a (see FIG. 1), in composite structures 218 (see FIG. 7), such as composite laminates 14, and to understand the benefits of variables that may be changed during testing.

In addition, disclosed embodiments of the test system 10 (see FIGS. 1, 2B, 2C, 4), and method 180 (see FIG. 6) provide for a composite laminate 14 with bulk portions 74 (see FIG. 1), such as air 74a (see FIG. 1), between the plies 66, which leads to fiber distortion 12 (see FIG. 1) when compacted with vacuum compaction 144 (see FIG. 1). The location of the fiber distortion 12 may be further controlled with the one or more fiber distortion initiators 90, or wrinkle initiators. The excess material 150 (see FIG. 1), such as the extra length of the fibers 72a (see FIG. 1) is not relieved during the pressurized cure process 140 (see FIG. 1) due to the fairing bars 40, or restrictor beams. The test system 10 (see FIGS. 1, 2B, 2C, 4) includes the plurality of fairing bars 40, such as the first fairing bar 40a (see FIG. 1) and the second fairing bar 40b (see FIG. 1) that constrain or restrict the plies 66 (see FIG. 1) of the composite laminate 14 (see FIG. 1) from expanding or stretching outwardly during cure, such as during the pressurized cure process 140 (see FIG. 1), and relieving the built-in residual stresses leading to no fiber distortion. Moreover, when the composite laminate 14 is compacted down with two caul plates 120 (see FIG. 1), with a gap in between the two caul plates, and the caul plates 120 on top of the composite laminate 14, during the pressurized cure process 140 (see FIG. 1), a pressure differential region 114 (see FIG. 1) is created at the location 92 (see FIG. 1) of the fiber distortion initiator 90 (see FIG. 1), leading to a distorted out-of-plane fiber 110 (see FIG. 1), such as a wrinkle 110a (see FIG. 1).

Many modifications and other embodiments of the disclosure will come to mind to one skilled in the art to which this disclosure pertains having the benefit of the teachings presented in the foregoing descriptions and the associated drawings. The embodiments described herein are meant to be illustrative and are not intended to be limiting or exhaustive. Although specific terms are employed herein, they are used in a generic and descriptive sense only and not for purposes of limitation.

What is claimed is:

1. A test system for creating controlled and repeatable out-of-plane fiber distortion in a composite laminate, the test system comprising:
   a curved layup tool comprising a layup portion having a layup surface with a curved configuration and a convex profile, the layup portion coupled to a base structure portion, and the curved layup tool being in a stationary position;
   two fairing bars attached to the layup surface and spaced opposite to one another;
   the composite laminate comprising a plurality of stacked plies, the composite laminate manually laid up on the layup surface of the curved layup tool and positioned between the two fairing bars;
   one or more fiber distortion initiators positioned at one or more locations under, and adjacent to, one or more plies of the plurality of stacked plies, each of the one or more fiber distortion initiators comprising a structure having a volume that increases a height of a portion of the one or more plies of the plurality of stacked plies stacked over each of the one or more fiber distortion initiators; and
   two caul plates positioned over the composite laminate and positioned between the two fairing bars, the two caul plates having a gap in between the two caul plates,
   wherein when the test system undergoes a pressurized cure process with a vacuum compaction, a restricted outward expansion of the plurality of stacked plies by the two fairing bars, and a pressure differential region formed by the one or more fiber distortion initiators at the one or more locations, create the controlled and repeatable out-of-plane fiber distortion of the one or more plies of the plurality of stacked plies in the composite laminate, at one or more controlled locations in the composite laminate, and
   further wherein the pressure differential region includes a low pressure area next to a high pressure area, the low pressure area and the high pressure area located above the one or more locations of the one or more fiber distortion initiators.

2. The test system of claim 1, further comprising a film layer positioned between the composite laminate and the two caul plates, wherein the film layer has a bottom side adjacent the composite laminate and a top side adjacent the two caul plates.

3. The test system of claim 1, wherein the two fairing bars comprise a first fairing bar and a second fairing bar, and the composite laminate has a first peripheral end abutting the first fairing bar and has a second peripheral end abutting the second fairing bar.

4. The test system of claim 1, wherein at least one of the one or more fiber distortion initiators is positioned adjacent to, and between, the layup surface of the curved layup tool and a first ply laid over the layup surface and the at least one fiber distortion initiator.

5. The test system of claim 1, wherein at least one of the one or more fiber distortion initiators is positioned adjacent to, and between, two plies of the plurality of stacked plies.

6. The test system of claim 1, wherein the one or more fiber distortion initiators comprises one of, a composite material overfill element, an outer mold line (OML) strip, an inner mold line (IML) strip, and a film layer.

7. The test system of claim 1, wherein each of the one or more fiber distortion initiators has a length that is substantially equal to a length of the composite laminate.

8. The test system of claim 1, wherein the two caul plates comprise a first caul plate positioned next to a second caul plate, with the gap in between the first caul plate and the second caul plate, prior to the test system undergoing the pressurized cure process.

9. The test system of claim 1, wherein the test system is a sub-scale test system for creating the controlled and repeatable out-of-plane fiber distortion at a sub-scale level that is representative of out-of-plane fiber distortion of a full-scale size part.

10. The test system of claim 9, wherein the curved layup tool of the sub-scale test system has a radius of curvature that is substantially equal to a part radius of curvature of the full-scale size part.

11. A test system for creating controlled and repeatable out-of-plane fiber distortion in a composite laminate, used for testing purposes and process improvement, the test system comprising:
   a curved layup tool comprising a layup portion having a layup surface with a curved configuration and a convex profile, the layup portion coupled to a base structure portion, and the curved layup tool being in a stationary position;

a first fairing bar and a second fairing bar, both attached to the layup surface, the first fairing bar spaced opposite the second fairing bar in a parallel alignment;

the composite laminate comprising a plurality of stacked carbon fiber plies, the composite laminate manually laid up on the layup surface of the curved layup tool, and the composite laminate having a first peripheral end abutting the first fairing bar and having a second peripheral end abutting the second fairing bar;

one or more fiber distortion initiators positioned at one or more locations under, and adjacent to, one or more carbon fiber plies of the plurality of stacked carbon fiber plies, each of the one or more fiber distortion initiators comprising a structure having a volume that increases a height of a portion of the one or more carbon fiber plies of the plurality of stacked carbon fiber plies stacked over each of the one or more fiber distortion initiators;

a first caul plate positioned next to a second caul plate with a gap in between the first caul plate and the second caul plate, the first caul plate and the second caul plate positioned over the composite laminate and positioned between the first fairing bar and the second fairing bar, the first caul plate and the second caul plate each having an outer side end abutting the first fairing bar and the second fairing bar, respectively; and a film layer positioned between the composite laminate and the first caul plate and the second caul plate, wherein the film layer has a bottom side adjacent the composite laminate and a top side adjacent the first caul plate and the second caul plate, wherein when the test system undergoes a pressurized cure process with a vacuum compaction, the first fairing bar and the second fairing bar restrict the plurality of stacked carbon fiber plies from expanding outwardly, and the one or more fiber distortion initiators create a pressure differential region at the one or more locations, to form distorted out-of-plane fibers at one or more controlled locations in the one or more carbon fiber plies of the plurality of stacked carbon fiber plies stacked over the one or more fiber distortion initiators, and, in turn, creating the controlled and repeatable out-of-plane fiber distortion in the composite laminate, used for testing purposes and process improvement, and further wherein the pressure differential region includes a low pressure area next to a high pressure area, the low pressure area and the high pressure area located above the one or more locations of the one or more fiber distortion initiators, and further wherein the test system is a sub-scale test system for creating the controlled and repeatable out-of-plane fiber distortion at a sub-scale level that is representative of out-of-plane fiber distortion of a full-scale size part comprising a fuselage barrel section of a fuselage of an aircraft.

12. The test system of claim 11, further comprising a third fairing bar and a fourth fairing bar, the composite laminate having a third peripheral end abutting the third fairing bar and having a fourth peripheral end abutting the fourth fairing bar.

13. The test system of claim 11, wherein at least one of the one or more fiber distortion initiators is positioned adjacent to, and between, the layup surface of the curved layup tool and a first ply laid over the layup surface and the at least one fiber distortion initiator.

14. The test system of claim 11, wherein at least one of the one or more fiber distortion initiators is positioned adjacent to, and between, two carbon fiber plies of the plurality of stacked carbon fiber plies.

15. A method for creating controlled and repeatable out-of-plane fiber distortion in a composite laminate, the method comprising the steps of:

assembling a test system comprising:
    a curved layup tool comprising a layup portion having a layup surface with a curved configuration and a convex profile, the layup portion coupled to a base structure portion, and the curved layup tool being in a stationary position;
    two fairing bars attached to the layup surface and spaced opposite to one another;
    the composite laminate comprising a plurality of stacked plies, the composite laminate manually laid up on the layup surface of the curved layup tool and positioned between the two fairing bars;
    one or more fiber distortion initiators positioned at one or more locations under, and adjacent to, one or more plies of the plurality of stacked plies, each of the one or more fiber distortion initiators comprising a structure having a volume that increases a height of a portion of the one or more plies of the plurality of stacked plies stacked over each of the one or more fiber distortion initiators; and
    two caul plates positioned over the composite laminate and positioned between the two fairing bars, the two caul plates having a gap in between the two caul plates;

curing the test system with a pressurized cure process and a vacuum compaction, to restrict, with the two fairing bars, the plurality of stacked plies from expanding outwardly, and to create, with the one or more fiber distortion initiators, a pressure differential region at the one or more locations, wherein the pressure differential region includes a low pressure area next to a high pressure area, the low pressure area and the high pressure area located above the one or more locations of the one or more fiber distortion initiators; and forming distorted out-of-plane fibers at one or more controlled locations in the one or more plies of the plurality of stacked plies stacked over the one or more fiber distortion initiators, to create the controlled and repeatable out-of-plane fiber distortion in the composite laminate.

16. The method of claim 15, further comprising using the test system and the controlled and repeatable out-of-plane fiber distortion for one or more of, testing purposes, and process improvement, for eliminating or minimizing out-of-plane fiber distortion in composite structures.

17. The method of claim 15, wherein assembling the test system comprises assembling the test system further comprising a film layer positioned between the composite laminate and the two caul plates, wherein the film layer has a bottom side adjacent the composite laminate and a top side adjacent the two caul plates.

18. The method of claim 15, wherein assembling the test system comprises assembling the test system with at least one of the one or more fiber distortion initiators positioned adjacent to, and between, the layup surface of the curved layup tool and a first ply laid over the layup surface and the at least one fiber distortion initiator.

19. The method of claim 15, wherein assembling the test system comprises assembling the test system with at least one of the one or more fiber distortion initiators positioned adjacent to, and between, two plies of the plurality of stacked plies.

20. The method of claim 15, wherein assembling the test system comprises assembling the test system comprising a sub-scale test system for creating the controlled and repeatable out-of-plane fiber distortion at a sub-scale level that is representative of out-of-plane fiber distortion of a full-scale size part.

* * * * *